(12) United States Patent
Liu et al.

(10) Patent No.: US 11,617,553 B2
(45) Date of Patent: Apr. 4, 2023

(54) LOCAL ENHANCEMENT FOR A MEDICAL IMAGE

(71) Applicant: GE Precision Healthcare LLC, Wauwatosa, WI (US)

(72) Inventors: James Zhengshe Liu, Cottonwood Heights, UT (US); Xiaosong Liu, Beijing (CN); Longjiang Yu, Beijing (CN); HongChang Ma, Beijing (CN); Jan D. Bruening, Salt Lake City, UT (US); Todd W. Brown, Tooele, UT (US)

(73) Assignee: GE Precision Healthcare LLC, Wauwatosa, WI (US)

(*) Notice: Subject to any disclaimer, the term of this patent is extended or adjusted under 35 U.S.C. 154(b) by 134 days.

(21) Appl. No.: 17/402,113

(22) Filed: Aug. 13, 2021

(65) Prior Publication Data

US 2023/0050772 A1 Feb. 16, 2023

(51) Int. Cl.
*A61B 6/00* (2006.01)
*G06T 7/00* (2017.01)
(Continued)

(52) U.S. Cl.
CPC .......... *A61B 6/469* (2013.01); *A61B 6/06* (2013.01); *A61B 6/4441* (2013.01); *A61B 6/463* (2013.01);
(Continued)

(58) Field of Classification Search
CPC ......... A61B 6/504; A61B 6/469; A61B 5/505; A61B 6/032; A61B 6/03; A61B 6/037; A61B 6/541; A61B 6/5247; A61B 6/545; A61B 6/06; A61B 6/465; A61B 6/5235; A61B 6/5205; A61B 6/5241;
(Continued)

(56) References Cited

U.S. PATENT DOCUMENTS 5,042,077 A 8/1991 Burke
5,542,003 A 7/1996 Wofford
(Continued)

FOREIGN PATENT DOCUMENTS

CN 105023273 A 11/2015
CN 107106097 A * 8/2017 ............... A61B 6/06
(Continued)

OTHER PUBLICATIONS

Borota et al., "Sport Region of Interest Imaging: A Novel Functionality Aimed at X-Ray Dose Reduction in Neurointerventional Procedures," Radiation Protection Dosimetry, vol. 188, Issue 3, Mar. 2020, pp. 322-331, Published Jan. 16, 2020, 10 pages.
(Continued)

*Primary Examiner* — Don K Wong

(57) ABSTRACT

The present disclosure relates to locally enhancing medical images. In accordance with certain embodiments, a method includes determining a boundary of a region of interest in a displayed medical image, overlaying the boundary on the displayed medical image, adjusting a position of a collimator of a medical imaging system based on the determined boundary, enhancing image quality of the region of interest, and displaying the enhanced region of interest within the boundary.

20 Claims, 20 Drawing Sheets

(51) Int. Cl.
   *G06K 9/62* (2022.01)
   *G06T 5/00* (2006.01)
   *G21K 1/04* (2006.01)
   *A61B 6/06* (2006.01)

(52) U.S. Cl.
   CPC ............ *A61B 6/5258* (2013.01); *G06T 5/002* (2013.01); *G06T 5/008* (2013.01); *G21K 1/04* (2013.01); *G06T 2207/10116* (2013.01); *G06T 2207/20104* (2013.01); *G06T 2207/30004* (2013.01)

(58) Field of Classification Search
   CPC ..... A61B 5/0037; A61B 6/463; A61B 6/5294; A61B 5/7445; A61B 5/7465; A61B 6/464; A61B 8/4416; A61B 6/4021; A61B 6/467; A61B 6/5229; A61B 6/54; G06T 2207/10081; G06T 2207/10116; G06T 2211/40
   See application file for complete search history.

(56) References Cited

U.S. PATENT DOCUMENTS

| | | | |
|---|---|---|---|
| 6,735,330 | B1 | 5/2004 | Van Metter |
| 6,768,784 | B1 | 7/2004 | Green |
| 7,218,763 | B2 | 5/2007 | Belykh |
| 7,340,033 | B2 | 3/2008 | Mollus |
| 8,861,886 | B2 | 10/2014 | Huo |
| 9,271,687 | B2 | 3/2016 | Koh |
| 9,460,499 | B2 | 10/2016 | McLaughlin |
| 2008/0152204 | A1 | 6/2008 | Huo |
| 2011/0123086 | A1 | 5/2011 | Nie |
| 2012/0032953 | A1 | 2/2012 | Schulz |
| 2012/0263366 | A1 | 10/2012 | Huo |
| 2014/0176554 | A1 | 6/2014 | Cohen |
| 2015/0139395 | A1 | 5/2015 | Yi |
| 2015/0348247 | A1 | 12/2015 | McLaughlin |
| 2016/0317104 | A1 | 11/2016 | Guez |
| 2019/0138192 | A1 | 5/2019 | Rao |
| 2019/0147639 | A1 | 5/2019 | Sudarsky |
| 2019/0286305 | A1 | 9/2019 | Sevenster |
| 2019/0343456 | A1 | 11/2019 | Kahlert |

FOREIGN PATENT DOCUMENTS

| | | |
|---|---|---|
| EP | 2767236 A1 | 8/2014 |
| WO | 2016135867 A1 | 9/2016 |

OTHER PUBLICATIONS

Yia, "Region-of-Interest Imaging with C-arm Computed Tomography," Doctoral Thesis, Published Mar. 29, 2016, Friedrich-Alexander-Universität Erlangen-Nürnberg (FAU), 164 pages.

* cited by examiner

US 11,617,553 B2

LOCAL ENHANCEMENT FOR A MEDICAL IMAGE

TECHNICAL FIELD

This disclosure relates to a system and method for enhancing a medical image and more particularly to a system and method for enhancing a medical image by locally adjusting a brightness and a contrast of a medical image.

BACKGROUND

Radiographic medical imaging systems may provide non-invasive means for imaging internal structures (i.e., bone, tissue, etc.) of a patient. A radiographic imaging system may include a C-arm coupled to a base that supports the C-arm, a radiation source, and a radiation detector. The C-arm supports the radiation source and the radiation detector opposite the radiation source. The C-arm rotates about an examination region that includes a portion of the patient and the radiation source emits radiation that traverses the examination region. The radiation detector detects the radiation that traverses the examination region and generates a signal indicative thereof. A reconstructor processes the signal and reconstructs image data indicative of the examination region and the portion of the patient within the examination region.

SUMMARY

In one embodiment, the present disclosure provides a method. The method includes determining a boundary of a region of interest in a displayed medical image, overlaying the boundary on the displayed medical image, adjusting a position of a collimator of a medical imaging system based on the determined boundary, enhancing image quality of the region of interest, and displaying the enhanced region of interest within the boundary.

In another embodiment, the present disclosure provides a system. The system includes a processor, a computer readable storage medium in communication with the processor, wherein the processor executes computer readable instructions stored in the computer readable storage medium which cause the processor to determine a boundary of a region of interest in a displayed medical image, overlay the boundary on the displayed medical image, adjust a position of a collimator of a medical imaging system based on the determined boundary, enhance image quality of the region of interest, and display the enhanced region of interest within the boundary.

In yet another embodiment, the present disclosure provides a computer readable storage medium with computer readable program instructions. When executed by a processor, the instruction cause the processor to determine a boundary of a region of interest in a displayed medical image, overlay the boundary on the displayed medical image, adjust a position of a collimator of a medical imaging system based on the determined boundary, enhance image quality of the region of interest, and display the enhanced region of interest within the boundary.

BRIEF DESCRIPTION OF THE DRAWINGS

Various aspects of this disclosure may be better understood upon reading the following detailed description with reference to the drawings in which.

Figure 1:
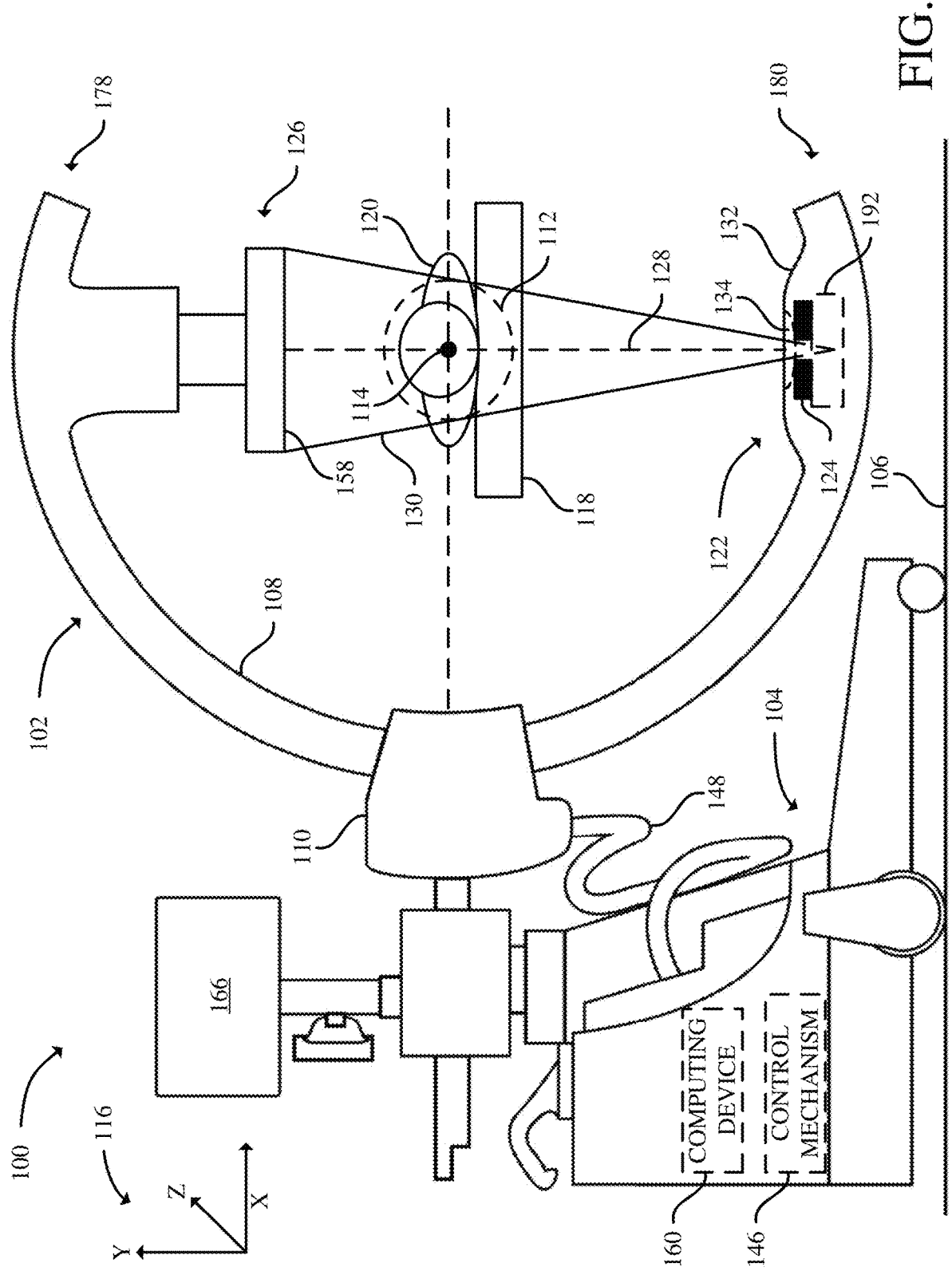
FIG. 1 depicts a medical imaging system in accordance with an exemplary embodiment.

The drawings illustrate specific acts of the described components, systems, and methods for locally enhancing a medical image. Together with the following description, the drawings demonstrate and explain the structures, methods, and principles described herein. In the drawings, the thickness and size of components may be exaggerated or otherwise modified for clarity. Well-known structures, materials, or operations are not shown or described in detail to avoid obscuring aspects of the described components, systems, and methods.

DETAILED DESCRIPTION

One or more specific embodiments of the present disclosure are described below. These described embodiments are only examples of the systems and methods for locally enhancing a medical image. The skilled artisan will understand that specific details described in the embodiments can be modified when being placed into practice without deviating from the spirit of the present disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (i.e., a material, element, structure, number, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

Medical imaging systems may include a C-shaped arm that carries a radiation source and a radiation detector. The C-shape of the arm allows a physician to access to a patient while the patient is being imaged. In order to obtain medical images of an internal structure at various angles, the C-shaped arm may be rotated to various positions. Medical images produced by such medical imaging systems may be produced and displayed in black and white, wherein pixels of the display are illuminated along a range of gray shades from black to white. The brightness of each pixel may correspond to a density of an object at a location corresponding to a given pixel. For example, in a medical image of a region of interest that includes tissue and bone, the bone may appear darker than the tissue as bone is denser than tissue. Current medical imaging systems a range of possible intensities (i.e., shades of gray) for illuminating pixels ranging from 0 (i.e., no illumination or black) to N (i.e., total illumination or white). In some systems the intensities range from 0 to 255. Accordingly, a display may receive intensity values ranging from 0 to 255 and may thereby produce 256 shades of gray.

Current medical imaging systems reconstruct an entire image across the entire possible intensities in order to produce an image. As such, the most dense object in an image may have the lowest intensity (and may appear as the darkest object in the image) and the least dense object may have the highest possible intensity (and may appear as the brightest object in the image). Since the intensity range for a given pixel, is determined based on all other intensities across the entire image, a region of interest within the medical image may appear as too dark or too bright for a physician to properly observe the region of interest. This may cause a patient to be reimaged thereby exposing the patient and a technician to additional radiation. Some embodiments of the present disclosure relate to a system and method for adjusting the brightness and contrast (i.e., by adjusting pixel intensity) within a region of interest. Providing a system and a method that adjusts the brightness and contrast of a region of interest may enhance image quality of a medical image thereby allowing a physician to properly observe the region of interest thereby reducing the need for subjecting the patient and technician to additional radiation.

A patient may undergo a medical imaging produced in order to produce a medical image of a limited region of interest. Unfortunately, the medical image may include more area than is needed to observe the region of interest and as such, more area of the patient is exposed to radiation than is necessary. Furthermore, radiation emitted by the medical imaging system when the patient is being imaged may scatter thereby exposing a technician to radiation as well.

In some medical imaging systems, a collimator collimates radiation emitted by a radiation source to produce a radiation beam with a predetermined shape. Some embodiments of the present disclosure relate to controlling a collimator based on a determined region of interest. Controlling a collimator based on a determined region of interest may limit an amount of radiation a patient and a technician is exposed to.

Referring to the figures generally, the present disclosure describes systems and methods for locally enhancing a medical image. The medical imaging system described herein (i.e., the medical imaging system depicted in FIG. 1) may be generally referred to as a radiographic medical imaging system.

Referring now to FIG. 1, a medical imaging system 100 is shown in accordance with an exemplary embodiment. As illustrated in FIG. 1, in some embodiments, the medical imaging system 100 includes a rotatable C-arm 102 that is connected to a base 104. The base 104 supports the C-arm 102 while the C-arm 102 is stationary and while the C-arm 102 is rotating. The base 104 supports the C-arm 102 on a ground surface 106 on which the medical imaging system 100 sits. The C-arm 102 includes a C-shaped portion 108 that is connected to an extended portion 110. The extended portion 110 is rotatably coupled to the base 104 which allows the C-arm 102 to rotate about an examination region 112 and a rotational axis 114. In one embodiment, the C-arm 102 may be configured to rotate at least 180° in opposing directions relative to the base 104. While the following describes the rotation of the C-arm 102 as rotating in the X and Y directions of the Cartesian coordinate system 116 (i.e., rotating the C-shaped portion such that opposing ends of the C-shaped portion 108 are closer to or further from the extended portion 110 in various positions), it is understood that the C-arm 102 may also rotate in the Z direction (i.e., rotating the C-shaped portion 108 are closer to or further from a head of a patient within the examination region 112 in various positions).

In one embodiment, the medical imaging system 100 may need to work with a patient support 118 (i.e., bed, table, etc.) that supports a patient 120 while at least a portion of the patient 120 is within the examination region 112. The medical imaging system 100 also includes a radiation source 122, a source collimator 124, and a radiation detector 126. The radiation source 122 and the radiation detector 126 are positioned at opposite ends of the C-shaped portion 108 of the C-arm 102 along axis 128, where axis 128 intersects and extends radially relative to the rotational axis 114 and the source collimator 124 is positioned between the radiation source 122 and the examination region 112. The C-shaped portion 108 may be rotated as descried above in order to adjust the position of the radiation source 122 and the radiation detector 126. Furthermore, in the embodiment depicted in FIG. 1, the position of the radiation detector 126 may be varied such that the radiation detector 126 is placed further from or closer to the radiation source 122.

During a medical imaging procedure, a portion of the patient 120 is within the examination region 112 and the radiation source 126 emits radiation 130. In one embodiment, the radiation source 122 includes an X-ray tube (not shown in FIG. 1) housed within a casing 132. The X-ray tube generates the radiation 130 which escapes the casing 132 via an outlet 134. The source collimator 124 may narrow the radiation 130 emitted by the radiation source. The source collimator 124 collimates the radiation 130 to have a predetermined geometrical shape. A portion of the radiation 130 passes through the source collimator 124, traverses the examination region 112 and is attenuated by the portion of the patient 120 that is within the examination region 112. Specifically, the radiation source 122 emits the radiation 130 towards the radiation detector 126 which is on the opposite end of the C-arm 102.

Figure 2:
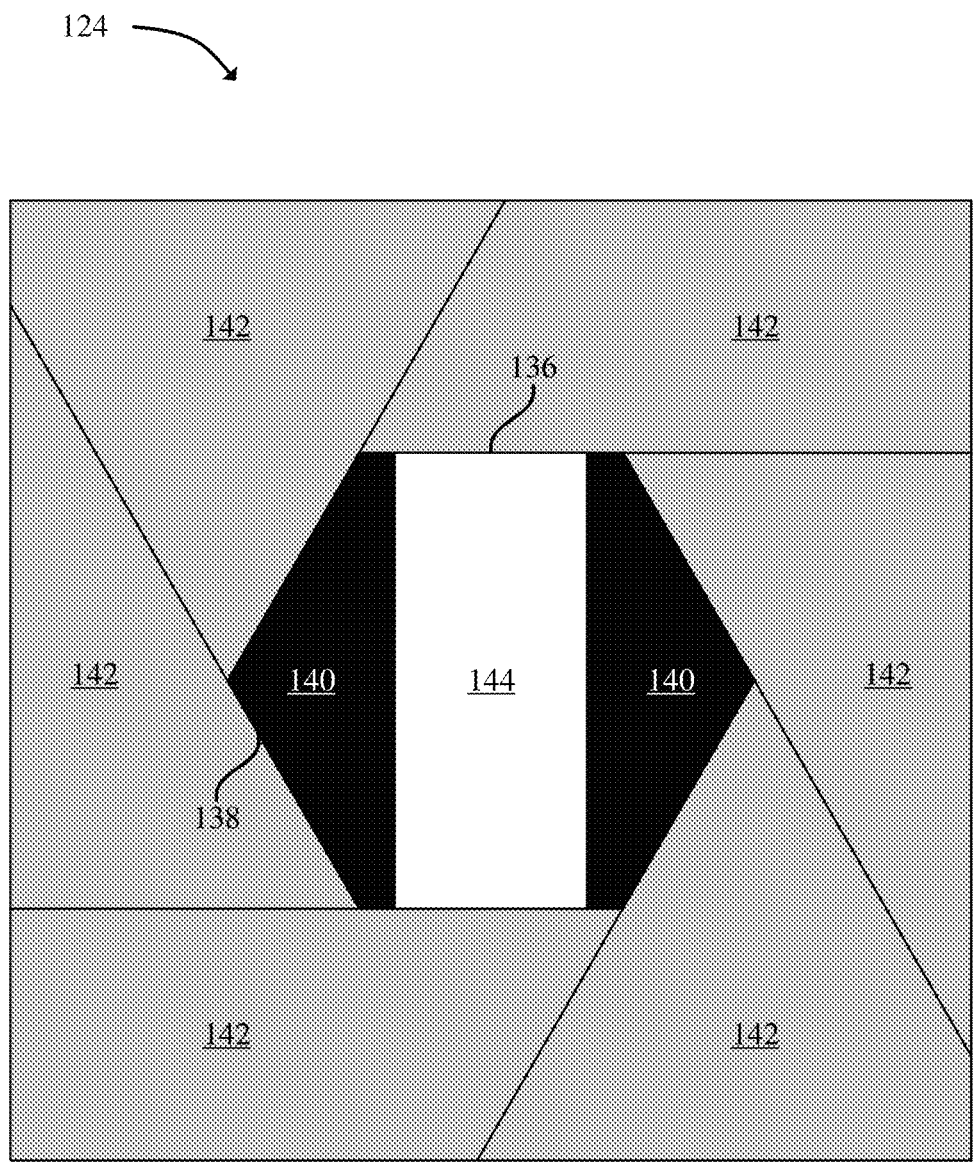
FIG. 2 depicts a source collimator of the medical imaging system in accordance with an exemplary embodiment.

Briefly turning to FIG. 2, the source collimator 124 is shown in accordance with an exemplary embodiment. In this embodiment, the source collimator 124 includes shutter 136 and an iris 138. The shutter 136 is defined by first collimator plates 140 and the iris 138 is defined by second collimator plates 142. The first collimator plates 140 and the second collimator plates 142 may be made of a material that is opaque to incoming radiation (i.e., lead, tungsten etc.). While FIG. 2 depicts the shutter 136 as including two first collimator plates 140 and depicts the iris 138 as including six second collimator plates 142 in other embodiments, the shutter 136 may include less than two first collimator plates 140 (i.e., one, three, four, etc.) and iris 138 may include more or less than six second collimator plates 142 (i.e., four, eight, ten, etc.). The first collimator plates 140 overlap with the second collimator plates 142. The first collimator plates 140 and the second collimator plates 142 are moveable and define a shape and size of an aperture 144 of the source collimator 124. The radiation 130 passes through the aperture 144 thereby shaping the radiation 130.

After passing the through the source collimator 124, the radiation 130 passes through a portion of the patient 120. The attenuated radiation is captured by the radiation detector 126. The radiation detector 126 includes a plurality of detector elements (not shown) that acquire projection data. Each detector element produces an electrical signal that is a measurement of the attenuation at the detector element location. The attenuation measurements form all the detector elements in the detector 126 are acquired separately to produce a transmission profile. In one embodiment, the radiation 126 is fabricated in a flat panel configuration that includes a plurality of detector elements.

When the radiation source 122 and the radiation detector 126 are rotated within the C-arm 102 within the object plane and around the patient 120, the angle at which the radiation 130 intersects the patient 120 changes. A group of attenuation measurements (i.e., projection data) from the radiation detector 126 at one C-arm 102 angle is referred to as a "view." A "scan" of the patient 120 includes a set of views made at different angles, or view angles, during rotation of the C-arm 102. As used herein the term view is not limited to the use described herein with respect to projection data from one C-arm 102 angle. The term view is used to mean one data acquisition whenever there are multiple acquisitions from different angles.

The medical imaging system 100 further includes as control mechanism 146 that is housed within the base 104. While FIG. 1 depicts the base 104 as including the control mechanism 146, in other embodiments the control mechanism 146 may be separate from the base 104 (i.e., in a different room). The control mechanism 146 is connected to the C-arm 102, the radiation source 122, and the radiation detector 126 via a cable 148 which allows the control mechanism to send data to/receive data from the C-arm 102, the radiation source 122, and the radiation detector 126. The control mechanism 146 controls the rotation of the C-arm 102 and the operation of the radiation source 122.

Figure 3:
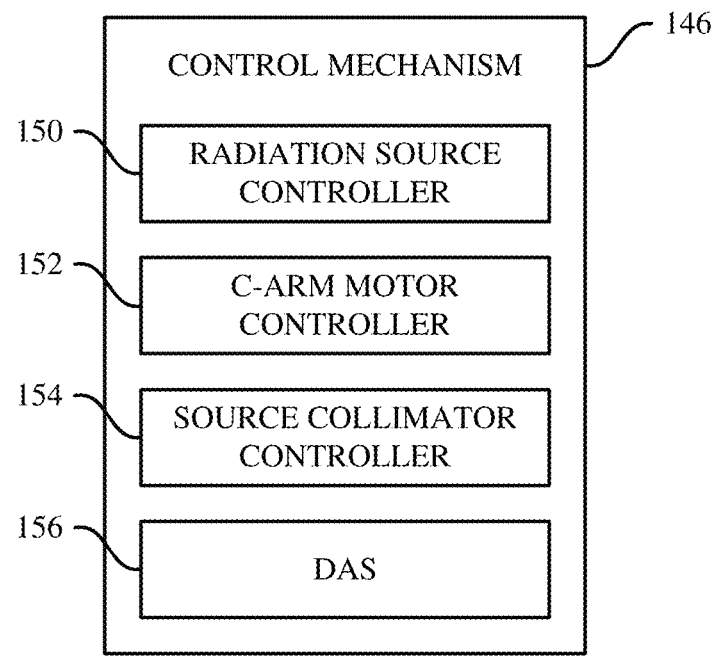
FIG. 3 is a block diagram of a control mechanism of the medical imaging system in accordance with an exemplary embodiment.

Briefly turning to FIG. 3, a block diagram of the control mechanism 146 is shown in accordance with an exemplary embodiment. In one embodiment, the control mechanism 146 includes a radiation source controller 150, a C-arm motor controller 152, and a source collimator controller 154. The radiation source controller 150 is configured to provide power and timing signals to the radiation source 122. The C-arm motor controller 152 controls the rotational speed and/or a position of the C-arm 102. Furthermore, the C-arm motor controller 152 controls the rotational axis 102, a position of the detector 126, and thereby controlling a source to detector distance, and a location of the patient support 118. The source collimator controller 154 is configured to control the size and the shape of the aperture 144 by controlling the position of the first collimator plates 140 and the second collimator plates 142. The control mechanism 146 further includes a data acquisition system (DAS) 156. The DAS 156 is configured to receive images from the radiation detector 126 and pass them for subsequent processing.

The C-arm 102 may be adjusted to a plurality of different positions by rotation of the C-shaped portion 108. For example, in an initial first position as shown in FIG. 1, the radiation detector may be placed vertically above the radiation source 122 relative to the surface 106 on which the medical imaging device 100 sits, with axis 128 arranged normal to the surface 106 intersecting a midpoint of the outlet 134 of the radiation source 122 and a midpoint of a detector surface 158 of the radiation detector 126. The C-arm motor controller 152 and a guide system within the extended portion 110 may adjust the C-shaped portion 108 from the first position to a different second position by rotating the C-shaped portion 108 via a coupling between the guide system and the C-shaped portion 108. In one example, the second position may be a position in which the radiation source 122 and the detector 126 are rotated 180° together relative to the first position such that the radiation source 122 is positioned vertically above the radiation detector 126 with axis 128 intersecting the midpoint of the outlet 134 and the midpoint of the detector surface 158. When adjusted to the second position, the radiation source 122 may be positioned vertically above the rotational axis 114 of the C-shaped portion 108 and the radiation detector 126 may be positioned vertically below the rotational axis 114.

The medical imaging device 100 further includes a computing device 160 that is housed within the base 104. While FIG. 1 depicts the computing device 160 as housed within the base 104, in other embodiments the computing device 160 may be remote from the rest of the imaging device 100. As used herein, a computing device (or system) is any device/system capable of processing, storing, and/or transmitting data (i.e., tablet, handheld device, smartphone, personal computer, laptop, network computer, server, mobile communication device, etc.). The computing device 160 may be connected to a network (i.e., a wide area network (WAN), a local area network (LAN), a public network (the internet), etc.) which allows the computing device 160 to communicate with other devices on a same network. In some embodiments, the network may be regarded as a private network and may include, for example, a virtual private network.

Figure 4:
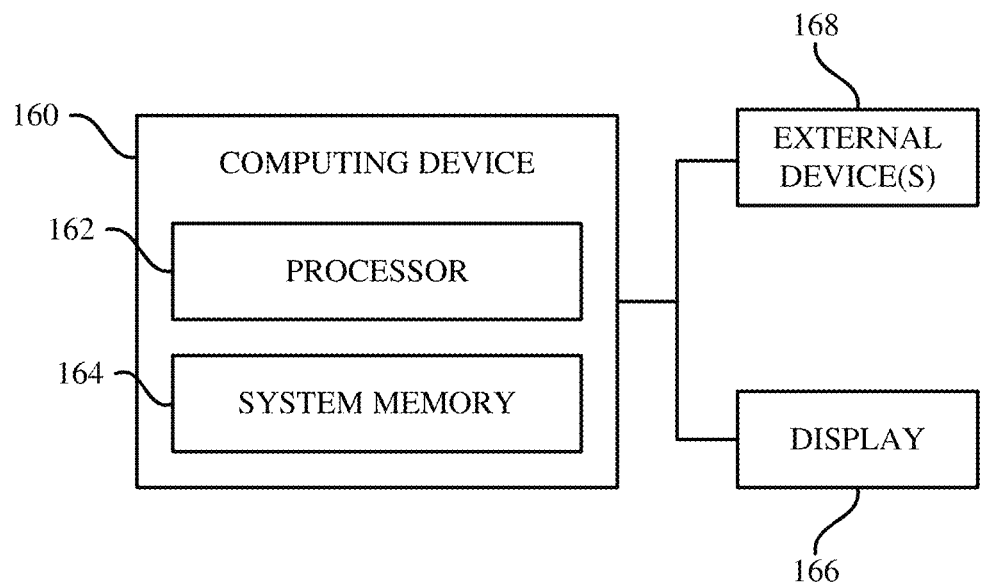
FIG. 4 is a block diagram of a computing system of the medical imaging system in accordance with an exemplary embodiment.

Briefly turning to FIG. 4, a block diagram of the computing device 160 is shown in accordance with an exemplary embodiment. The computing device 160 includes a processor 162 and a system memory 164. The processor is in communication with the system memory 164 and may execute computer readable program instructions stored in the system memory 164. As used herein, a processor may include a central processing unit (CPU), or other electronic components capable or executing computer readable program instructions (i.e., a digital signal processor, a field-programmable gate array (FPGA), a graphics processing unit (GPU), etc.). Furthermore, as used herein, a processor may include two or more of a CPU, a digital signal processor, an FPGA, and a GPU.

The system memory 164 is a computer readable storage medium. As used herein, a computer readable storage medium is any device that stores computer readable program instructions for execution by a processor and is not construed as transitory per se. Computer readable program instructions include programs, logic, data structures, modules, etc. that when executed by a processor create a means for implementing functions/acts. Computer readable program instructions when stored in a computer readable storage medium and executed by a processor direct a computer system and/or another device to function in a particular manner such that a computer readable storage medium comprises an article of manufacture. System memory as used herein includes volatile memory (i.e., random access memory (RAM) and dynamic RAM (DRAM)) and non-volatile memory (i.e., flash memory, read-only memory (ROM), magnetic computer storage devices, etc.). In some embodiments the system memory 164 may further include cache.

In one embodiment, the various methods and processes (i.e., the method described below with reference to FIGS. 8 and 19) may be stored as computer readable program instructions in the system memory 164. In this embodiment, the system memory 164 includes computer readable program instructions for locally enhancing a medical image.

In some embodiments, the computing device 160 is connected to a display 166 and one or more external devices 168. The external devices 168 include devices that allow a user to interact with/operate the computing device 160 (i.e., mouse, keyboard, touchscreen, speakers, etc.). In some embodiments, the display 166 displays a graphical user interface (GUI). The GUI includes editable fields for inputting data (i.e., patient data, imaging parameters, etc.) and further includes selectable icons. Selecting an icon and/or inputting data causes the processor 162 to execute computer readable program instructions stored in the system memory 164 which causes the processor to perform a task. For example, a user of the computing device 160 may use an external device 168 to select a "start" icon or the like which causes the processor 162 to being a medical imaging procedure.

While FIG. 1 illustrates only one computing device 160, in some embodiments, the medical imaging system 100 may include more than one computing device 160. The computing device 160 may be used for inputting or outputting imaging parameters, requesting examinations, plotting data, and/or viewing images. Furthermore, in certain embodiments, the medical imaging system 100 may be coupled to multiple displays, printers, workstations, and/or similar devices located either locally or remotely (i.e., within an institution or hospital or in a an entirely different location, etc.) via one or more configurable wired and/or wireless networks. Furthermore, in some embodiments, the base 104 further houses an internal power source (not shown) that provides electrical power to operate the medical imaging system 100. Alternatively, the base 104 may be connected to an external power source to power the medical imaging system 100. A plurality of connection cables may (i.e., cable 148) may be provided to transmit electrical power to the radiation source 122, the radiation detector 126, etc.

The computing device 160 is in communication with and provides commands to the radiation source controller 150, the C-arm motor controller 152, the source collimator controller 154, and the DAS 156 for controlling system operations such as data acquisition and/or data processing. In some embodiments, the computing device 160 controls operation of the radiation source controller 150, the C-arm motor controller 152, the source collimator controller 154, and the DAS 156 based on a user input.

Figure 5:
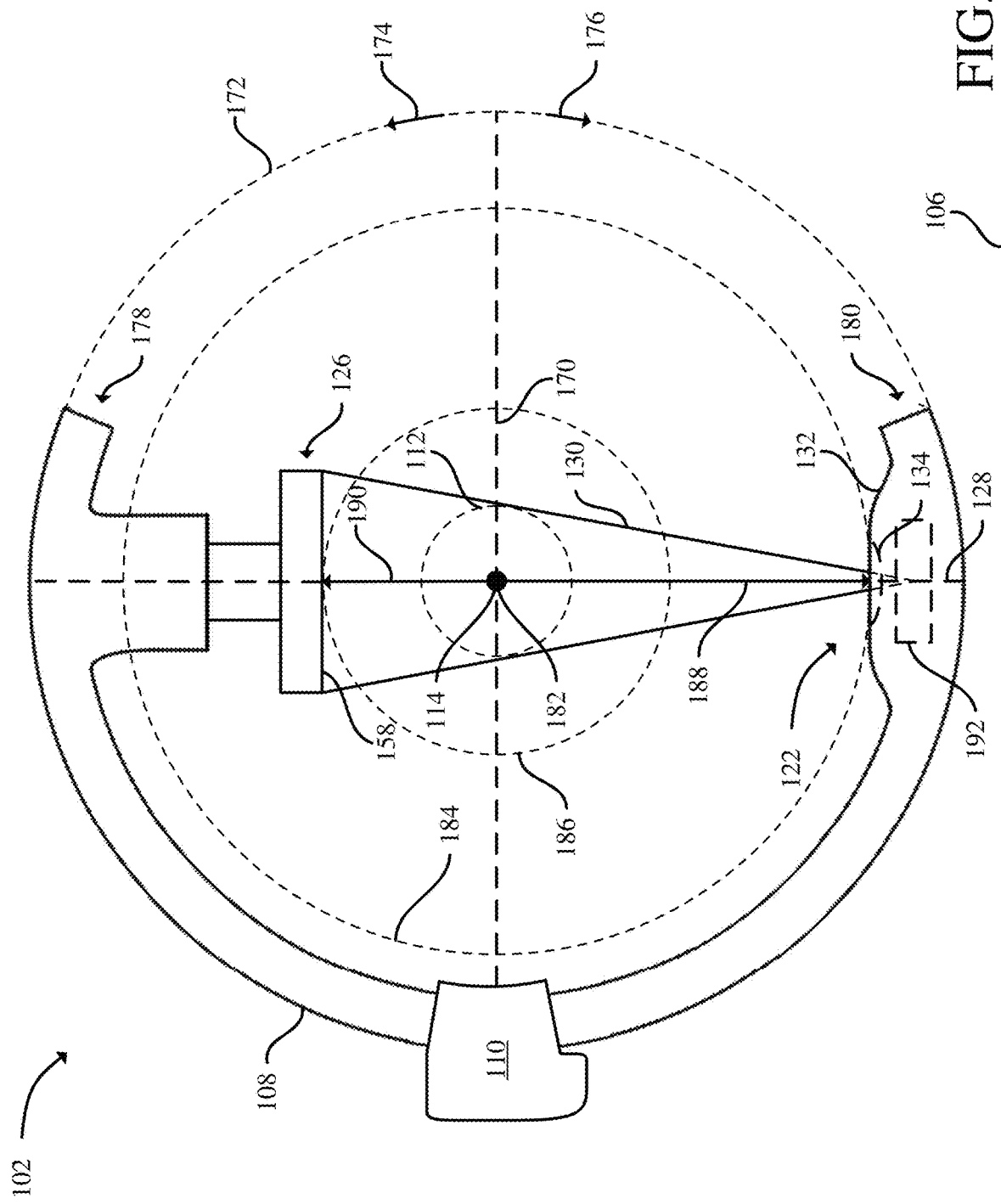
FIG. 5 depicts a C-arm of the medical imaging system in a first position in accordance with an exemplary embodiment.
Figure 7:
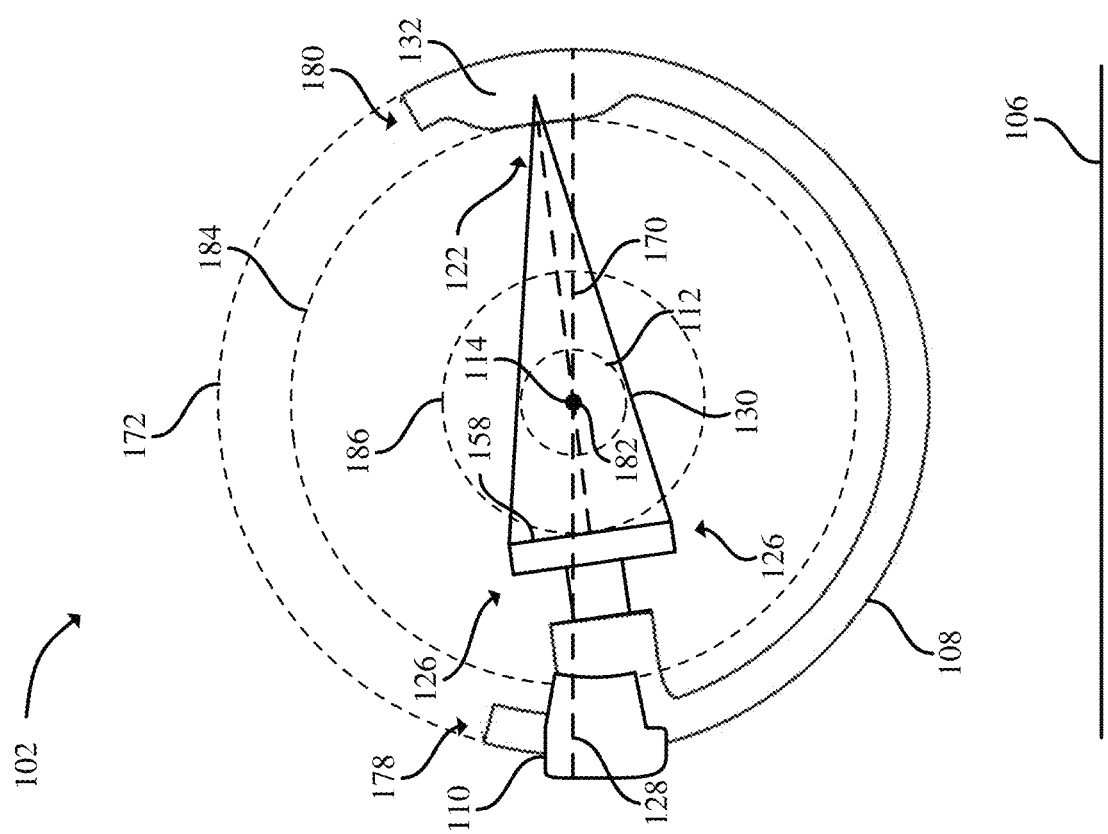
FIG. 7 depicts a C-arm of the medical imaging system in a third position in accordance with an exemplary embodiment
Figure 6:
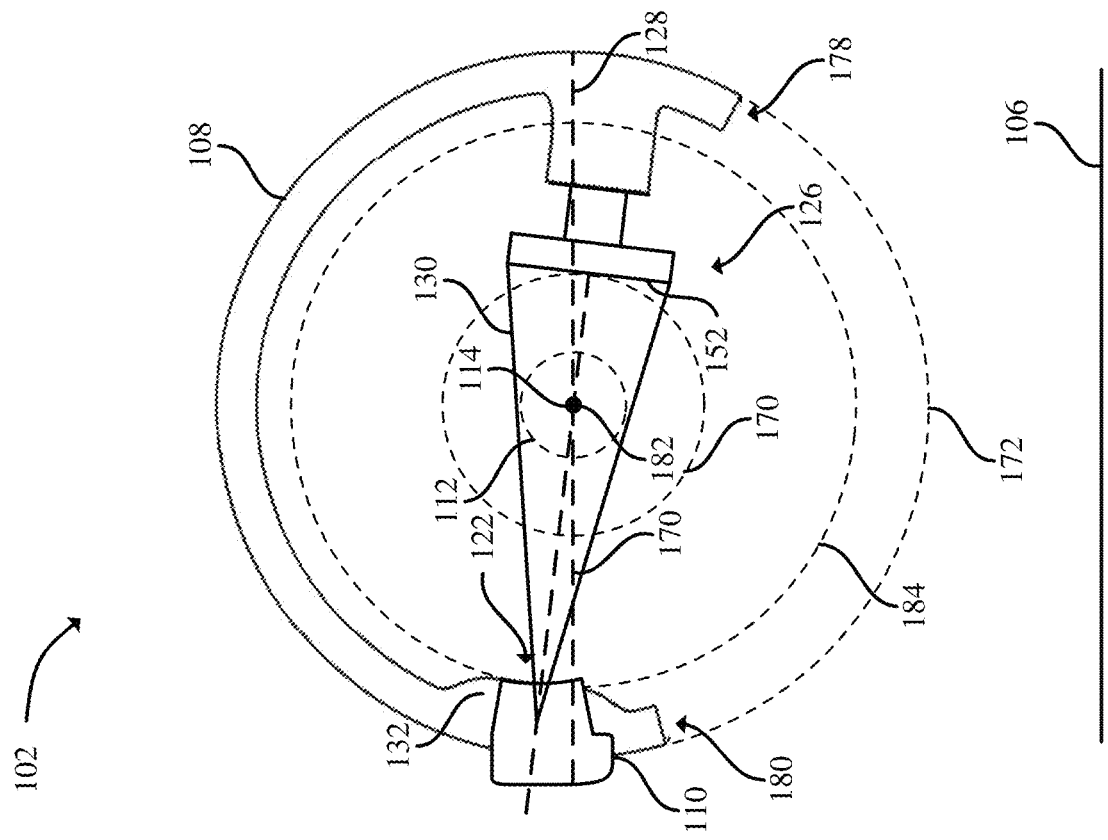
FIG. 6 depicts a C-arm of the medical imaging system in a second position in accordance with an exemplary embodiment.

For example, the computing device 160 may send a signal to the C-arm motor controller 152 which causes the C-arm motor controller 152 to rotate the C-shaped portion 108. Referring collectively to FIGS. 5-7, various example positions of the C-arm 102 are shown. In FIGS. 5-7, the base 104 and the cable 148 have been omitted and in FIGS. 6 and 7 the outlet 134 and the source collimator 124 has also been omitted for clarity.

Specifically, FIG. 5 shows the C-arm 102 in a first position in which the axis 128 between the detector surface 158 and the outlet 134 is arranged perpendicular to the ground surface 106 on which the medical imaging system 100 sits. Furthermore, as depicted in FIGS. 1 and 5, in the first position, the axis 128 is perpendicular to a horizontal axis 170. The horizontal axis 170 is parallel to the ground surface 106. FIG. 6 depicts the C-arm 102 in a second position in which the C-arm shaped portion 108 has been rotated. In the second position, the radiation source 122 is positioned closer to the extended portion 110 and the radiation detector 126 is positioned further from the extended portion 110 relative to the first position as shown by FIG. 5. FIG. 7 depicts the C-arm 102 in a third position in which the C-shaped portion 108 has been rotated. In the third position, the radiation source 122 is positioned further from the extended portion 110 and the radiation detector 126 is positioned closer to the extended portion 110 relative to the first position as shown by FIG. 5.

A rotational range of the C-shaped portion (i.e., an amount of angle through which the C-shaped portion 108 may rotate relative to the base unit 104) may be greater than 180°. For example, FIG. 6 may correspond to a rotation of the C-shaped portion 108 by an angle of approximately 95° around the rotational axis 114 relative to the position shown by FIGS. 1 and 5 may correspond to a rotation of the C-shaped portion 108 by an angle of approximately −95° around the rotational axis 114 relative to the position shown by FIG. 5, with the C-shaped portion 108 rotating through 190° to adjust from the position shown by FIG. 6 to the position shown by FIG. 7. In each of FIGS. 5-7, the extended portion 110 is maintained in position relative to the C-shaped portion 108, with the position of extended portion 110 in FIGS. 5-7 being the same as the position of extended portion 110 shown in FIG. 1 (i.e., with the extended portion 110 not rotated relative to the ground surface 106 or horizontal axis 170).

The radiation source 122 emits the radiation 130 towards the radiation detector 126. As the C-shaped portion 108 rotates around the rotational axis 114 (i.e., while imaging the patient 120), the radiation 130 remains directed toward the radiation detector 126 due to the concurrent rotation of each of the radiation source 122 and the radiation detector 126 around the rotational axis 114. While rotating around the rotational axis 114, the C-shaped portion 108 may move along path 172 in a first direction 174 or a second direction 176. Since the radiation source 122 and the radiation detector 126 rotate around the rotational axis 114 with the C-shaped portion 108, the radiation 130 emitted by the radiation source 122 passes through the examination region 112.

While stationary or rotating, a first end 178 and a second end 180 of the C-shaped portion 108 are positioned a same distance from a center 182 of the C-shaped portion 108. The center 182 of the C-shaped portion 182 shares a same position as the rotational axis 114. For example, the C-shaped portion 108 may have a uniform radius of curvature in a direction around the center 182 (i.e., a same radius of curvature at each location along the C-shaped portion 108 in the direction around the center 182) such that the first end 178 and the second end 180 are positioned a same distance from the center 182 of the C-shaped portion 108 along the axis 128. As such, the path 172 has a same curvature and radius as the C-shaped portion 108.

As described above, the C-shaped portion 108 may rotate around the rotational axis 114. In some embodiments, C-shaped portion 108 may also rotate about horizontal axis 170. In this configuration, the C-shaped portion 108 may rotate around either of rotational axis 114 or horizontal axis 170 (or both of rotational axis 114 and horizontal axis 170), where horizontal axis 170 is orthogonal to the rotational axis 114. In the views shown by FIGS. 5-7, however, the C-shaped portion 108 is rotated only around the rotational axis 114 and not the horizontal axis 170.

Although the first end 178 and second end 180 may be positioned the same length from the center 182, each of outlet 134 and detector surface 158, may be positioned at different lengths from the center 182 since the position of the detector 126 may be varied. For example, a rotational path 184 of the outlet 134 and a rotational path 186 of the radiation detector surface 158 may be different, with each of rotational path 184 and rotational path 186 being of circular shape. The outlet 134 may move along rotational path 184 and detector surface 158 may move along rotational path 186 during conditions in which the C-shaped portion 108 is rotated around rotational axis 114 (i.e., while the patient 120 is being imaged). However, a length 188 (i.e., a diameter of the rotational path 184) may be a longer length from the center 182 to the outlet 134 than a length 190 (i.e., a diameter of the rotational path 186) from the center 182 to the detector surface 158. In one embodiment, the length 188 may be larger than the length 190 due to the radiation source 122 being seated within the C-shaped portion 108. For example, in the embodiment depicted in FIG. 5, the radiation source 122 includes an X-ray tube 192. In this embodiment, the X-ray tube 192 may be housed within casing 132 and seated within the C-shaped portion 108. For the sake of clarity, the X-ray tube 192 has been omitted in FIGS. 6 and 7.

Positioning the X-ray tube 192 within the C-shaped portion 108 may enable the outlet 134 to be positioned closer to the second end 180 compared to configurations in which an X-ray tube 192 is not seated within the C-shaped portion 108, which may result in a decreased height of the radiation source 122 as a height of the radiation source 122 may be limited by the casing 132. The resulting reduced height of the radiation source 122 may increase an amount of open space between the detector surface 158 and the outlet 134, which may enable the C-arm 102 to accommodate larger patients and/or increase ease of use of the C-arm 102. Furthermore, in some embodiments, the seated position of the radiation source 122 within the C-shaped portion 108 may increase a balance of the C-arm 102, which may reduce undesired vibration of the C-arm 102. Positioning the radiation source 122 within the C-shaped portion 102 may also increase a balance of the C-arm 102 while the C-shaped portion 108 is rotating (i.e., while the patient 120 is being imaged) and may provide a counter weight to the radiation detector 126 which may reduce a load and/or vibration of a motor of the medical imaging system 100.

Returning to FIG. 1, in one embodiment, the medical imaging system 100 includes, or is coupled to a picture archiving and communication system (PACS). In an exemplary implementation, the PACS may be further coupled to a remote system such as a radiology department information system, hospital information system, an internal and/or an external network, etc. to allow operators at different locations to supply commands, parameters, and/or gain access to image data generated by the medical imaging system 100.

The medical imaging system 100 further includes or is coupled to an image reconstructor. Subsequently, the image reconstructor uses the sampled and digitized X-ray data to perform high-speed reconstruction. In certain embodiments, the image reconstructor may form part of the computing device 160. Alternatively, the image reconstructor may be omitted and instead the computing device 160 may perform one or more functions of the image reconstructor. Moreover, the image reconstructor may be located locally or remotely and may be operatively coupled to the medical imaging system 100 via a wired or wireless network. Particularly, in one embodiment, the reconstructor may use computing resources in a "cloud" network cluster for image reconstruction.

In some embodiments the reconstructor receives projection data and the projection data undergoes preprocessing and calibration to condition the data to represent the line integrals of attenuation coefficients of the patient 120. The processed data is commonly referred to as "projections." The acquired sets of projection data may be used for basis material decomposition (BMD). During BMD, the measured projections are converted to a set of material-density projections. The material-density projections may be reconstructed to form a pair or set of material-density maps or images of each respective basis material (i.e., bone, tissue, and/or contrast agents, etc.). The density maps or images may be, in turn, associated to form a volume rendering of the basis material in the imaged volume.

The projection data is processed to reconstruct an image that corresponds to a two-dimensional slice taken through the patient 120, or in some examples wherein the projection data includes multiple views or scans, a three-dimensional rendering of a portion of the patient 120. Once reconstructed, a basis material image reveals internal features of the patient 120 expressed by the densities of the materials. The image may be displayed to show these features. Once displayed, a practitioner may view the image to make a medical diagnosis or to discern characteristics of a feature of interest (i.e., lesion, organ, etc.).

As used herein, the phrase "reconstructing an image" is not intended to exclude embodiments in which data representing an image is generated but a viewable image is not. Therefore, as used herein, the term image broadly refers to both viewable images and data representing a viewable image. However, some embodiments described herein generate (or are configured to generate) at least one viewable image.

In one embodiment, the reconstructor stores reconstructed images in the system memory 164. In another embodiment, the reconstructor transmits the reconstructed image(s) to the computing device 160 for generating useful patient information for diagnosis and evaluation. In certain embodiments, the computing device 160 may transmit reconstructed images and/or patient informant to the display 166. In other embodiments, the reconstructed images may be transmitted from the system memory 164 or the reconstructor to the PACS for short-term or long-term storage.

Figure 8:
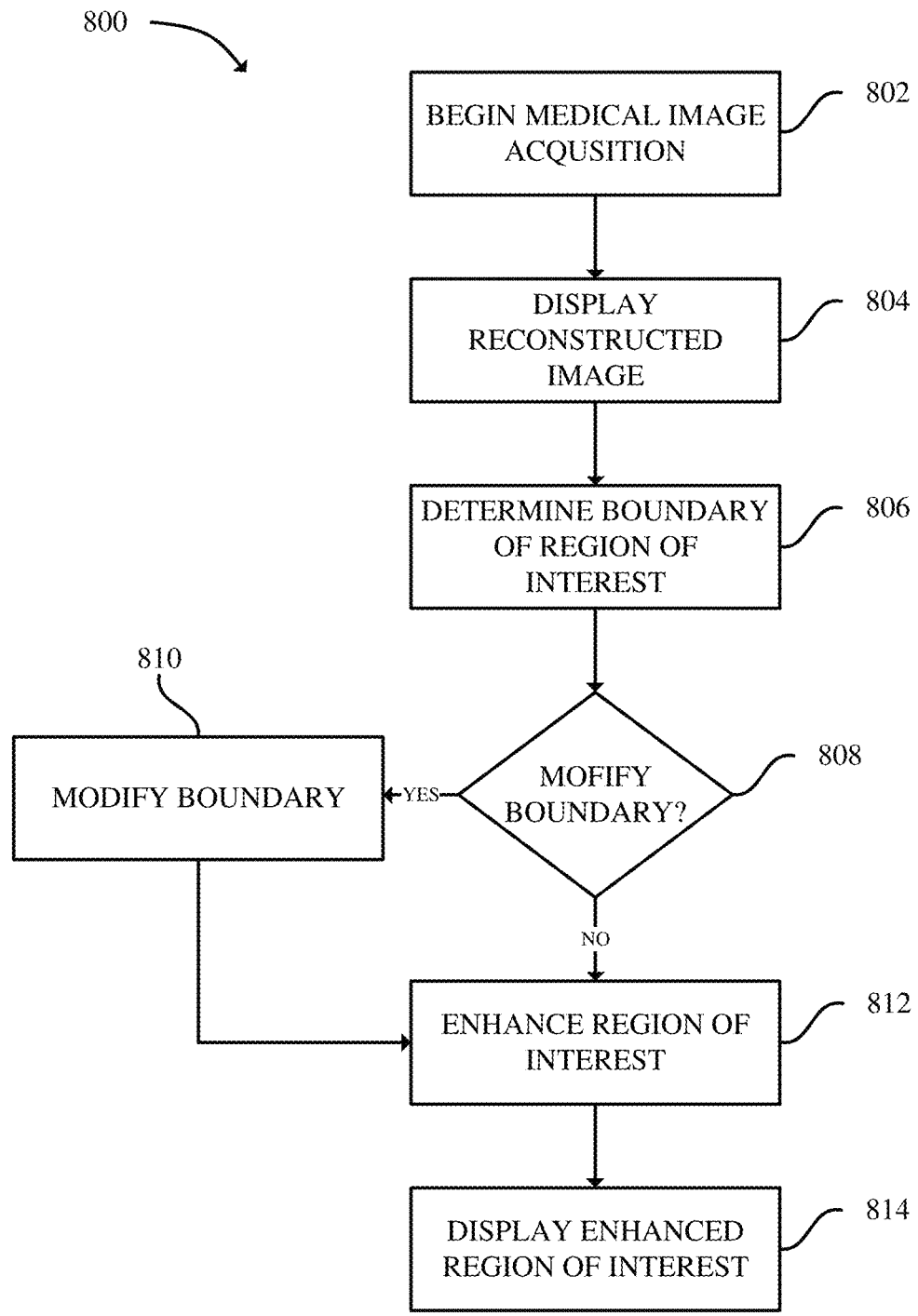
FIG. 8 is a flow chart of a method for locally enhancing a medical image in accordance with an exemplary embodiment.

Turning to FIG. 8, a method 800 for locally enhancing a medical image is shown in accordance with an exemplary embodiment. Various aspects of the method 800 depicted in FIG. 8 and the method 1900 depicted in FIG. 19 may be carried out by a "configured processor." As used herein, a configured processor is a processor that is configured according to an aspect of the present disclosure. In some embodiments, the processor 162 is a configured processor(s). The computer readable program instructions, that when executed by a configured processor, cause a configured processor to carry out the steps of the method 800 and the method 1900 are stored in a computer readable storage medium, including, but not limited to, the system memory 164.

At 802, a configured processor sends a signal to begin medical image acquisition to the control mechanism 146. In response to receiving the signal to begin medical image acquisition, the control mechanism 146 causes the medical imaging system 100 to begin acquiring projection data of the patient 120 as previously described herein. In one embodiment, the configured processor sends the signal to begin medical image acquisition in response to a user selecting an imaging protocol and/or a start icon or the like displayed in a GUI that is shown by the display 166. Furthermore, the signal to begin medical image acquisition includes imaging parameters (i.e., radiation source power and timing parameters, C-arm rotational speed and position parameters, etc.). In response to receiving the signal to begin medical image acquisition, the control mechanism 146 controls the position of the C-arm 102 and the operation of the radiation source 122 as a function of the received parameters which causes the medical imaging system 100 to acquire projection data of an internal anatomy (i.e., organ, bone, tissue, etc.) of the patient 120.

At 804, the configured processor reconstructs an image from the projection data as previously discussed herein and sends the reconstructed image to the display 166. In response to receiving the reconstructed image, the display 166 displays the image. Each pixel in the displayed image has a grayscale intensity ranging from 0-N which corresponds to a material density at a corresponding location within the imaged anatomy, wherein 0 pixel intensity corresponds to a black pixel (i.e., the most dense material within the image) and N correspond to a white pixel (i.e., the least dense material within the image). In one embodiment, each pixel in the displayed image has a grayscale intensity ranging from 0-255.

Figure 9:
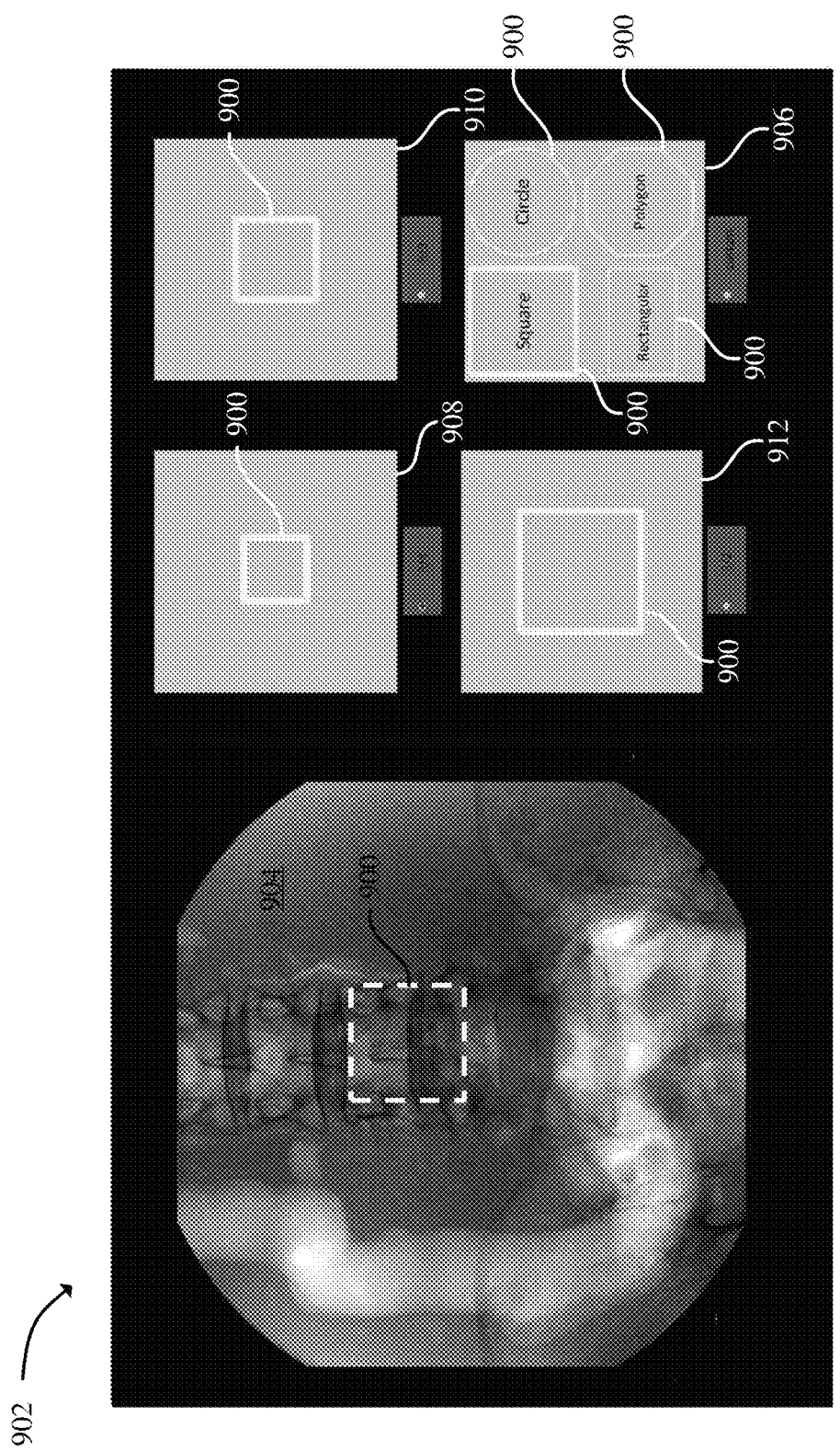
FIG. 9 depicts a graphical user interface with different sizes and shapes for a boundary that defines a region of interest in accordance with an exemplary embodiment.

At 806, the configured processor determines a shape and size of a boundary of a region of interest and overlays the determined boundary on the displayed image. In one embodiment, the configured processor determines the shape and size of the boundary of a region of interest based on a user selecting a predetermined shape and size. Briefly turning to FIG. 9, in one embodiment, the display 166 may display a graphical user interface (GUI) 902. The GUI 902 may include a first window 904 that displays the reconstructed image, a second window 906 that displays a plurality of predetermined shapes of a boundary 900 of a region of interest, a third window 908 that displays a first size of the boundary 900, a fourth window 910 that displays a second size of the boundary 900, and a fifth window 912 that displays a third size of the boundary 900. While FIG. 9 depicts the second window 906 as displaying a square, rectangle, circle, and an octagon shape boundary 900, the second window 906 may display other shapes for the boundary 900 (i.e., triangle, rhombus, hexagon, etc.).

A user may use an external device 168 (i.e., a mouse, touchscreen, etc.) to select one of the shapes of the boundary 900 displayed in the second window 906. In response the user selecting a shape of the boundary 900, the configured processor causes the display 166 to display varying sizes of the selected shape in the third window 908, the fourth window 910, and the fifth window 912. In one example, in response to a user selecting a circular boundary 900, the configured processor causes the display 166 to display a circular boundary 900 with varying sizes in the third window 908, the fourth window 910, and the fifth window 912. In another example, in response to a user selecting a rectangular boundary 900, the configured processor causes the display 166 to display a rectangular boundary 900 with varying sizes in the third window 908, the fourth window 910, and the fifth window 912.

A user may then use an external device 168 (i.e., a mouse, touchscreen, etc.) select a boundary 900 in one of the third window 908, the fourth window 910, and the fifth window 912. In response to the user selecting a boundary 900, the configured processor overlays the selected boundary 900 on the displayed reconstructed image in the first window 904 and causes the display 166 to display the reconstructed image with the overlaid boundary 900. The region within the boundary 900 is hereinafter referred to as a region of interest. In one embodiment, the configured processor automatically overlays the boundary 900 at a center of the displayed reconstructed image.

Figure 10:
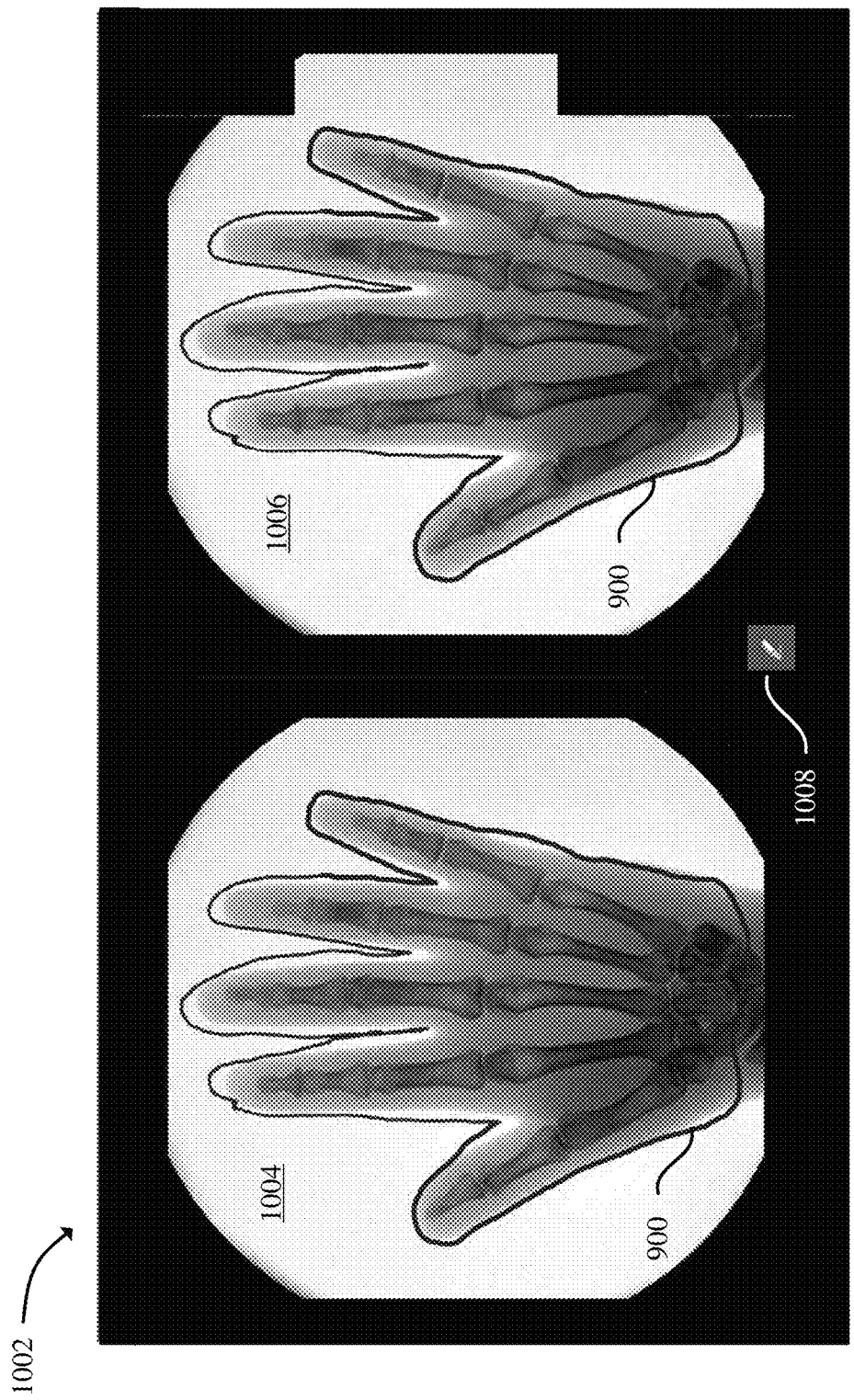
FIG. 10 depicts another graphical with user drawn boundary that defines a region of interest in accordance with an exemplary embodiment.

In another embodiment the configured processor determines the shape and size of the boundary of a region of interest based on a user drawing a boundary on a displayed reconstructed image. Briefly turning to FIG. 10, in another embodiment, the display 166 may display a GUI 1002. The GUI 1002 may include a first window 1004 that displays the reconstructed image and a second window 1006 that also displays the reconstructed image. Furthermore, the GUI 1002 may also include a pen icon 1008. After selecting the pen 1008, a user may use an external device 168 (i.e., a mouse, touchscreen, etc.) to draw the boundary 900 in the second window 1006. In response to the user drawing the boundary 900 in the second window 1006, the configured processor overlays the boundary 900 on the displayed reconstructed image in the first window 1004.

Figure 11:
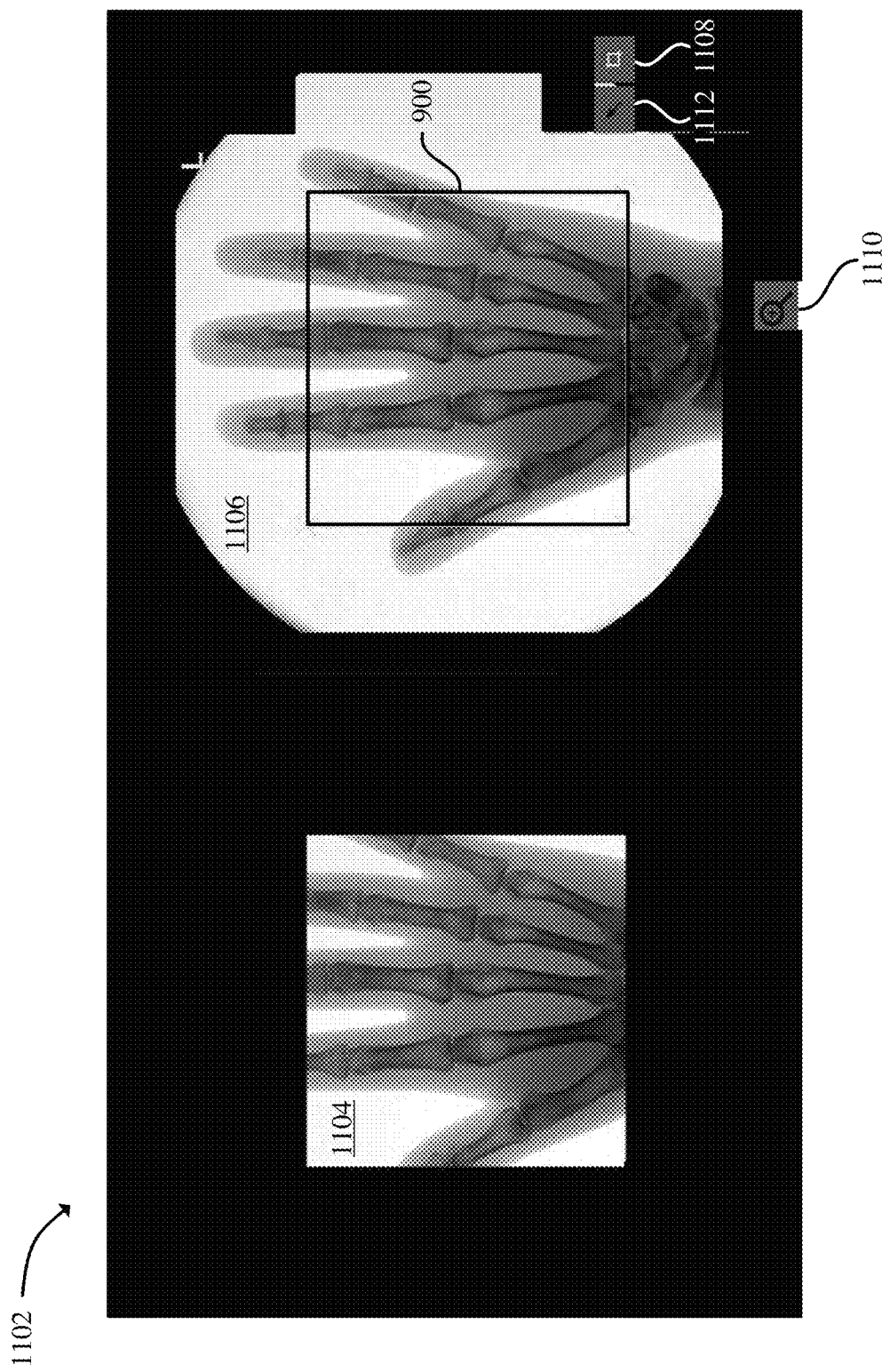
FIG. 11 depicts another graphical user interface with a cropped boundary that defines a region of interest in accordance with an exemplary embodiment.
Figure 12:
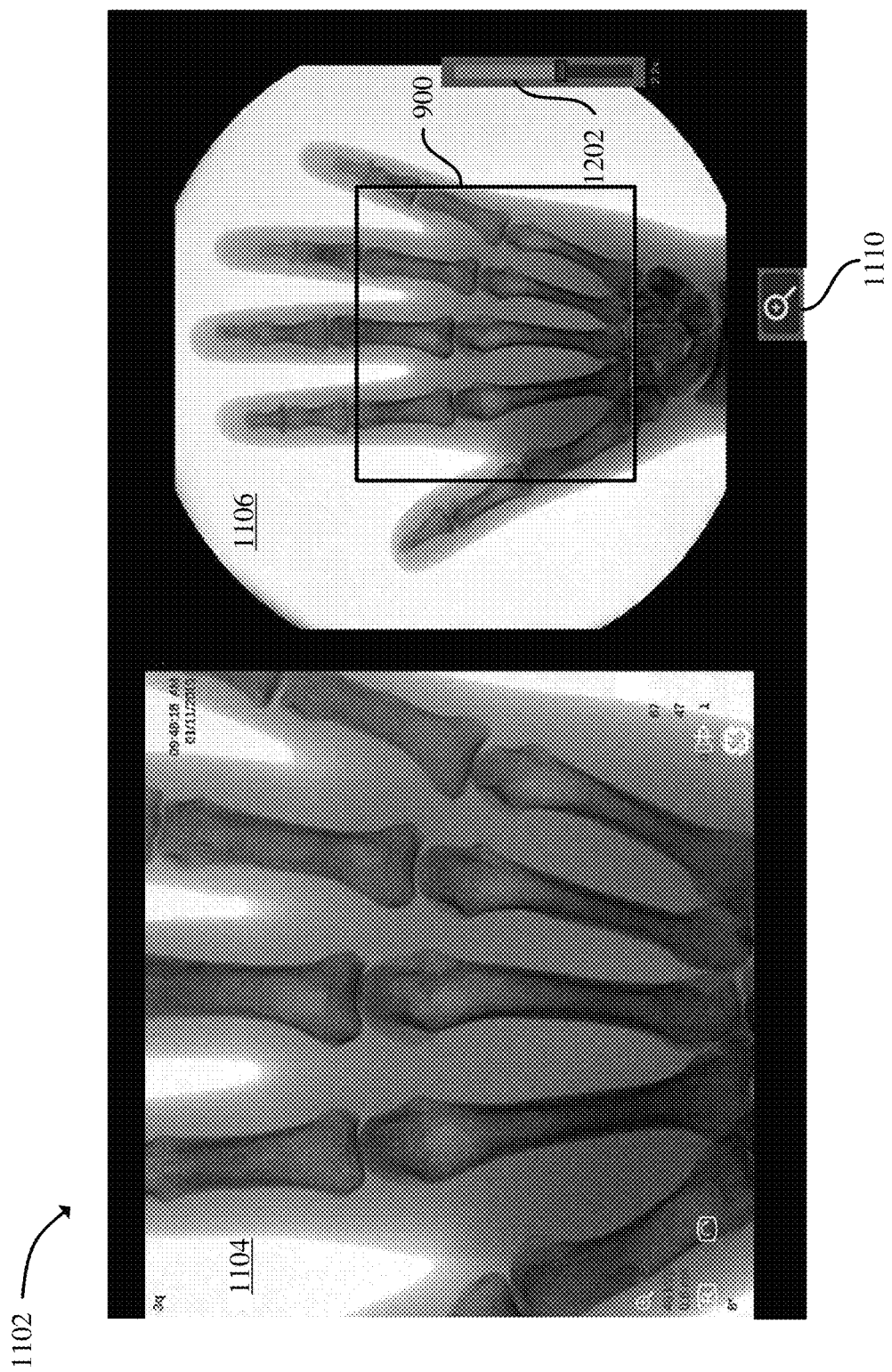
FIG. 12 depicts another graphical user interface with a zoom boundary that defines a region of interest in accordance with an exemplary embodiment.
Figure 13:
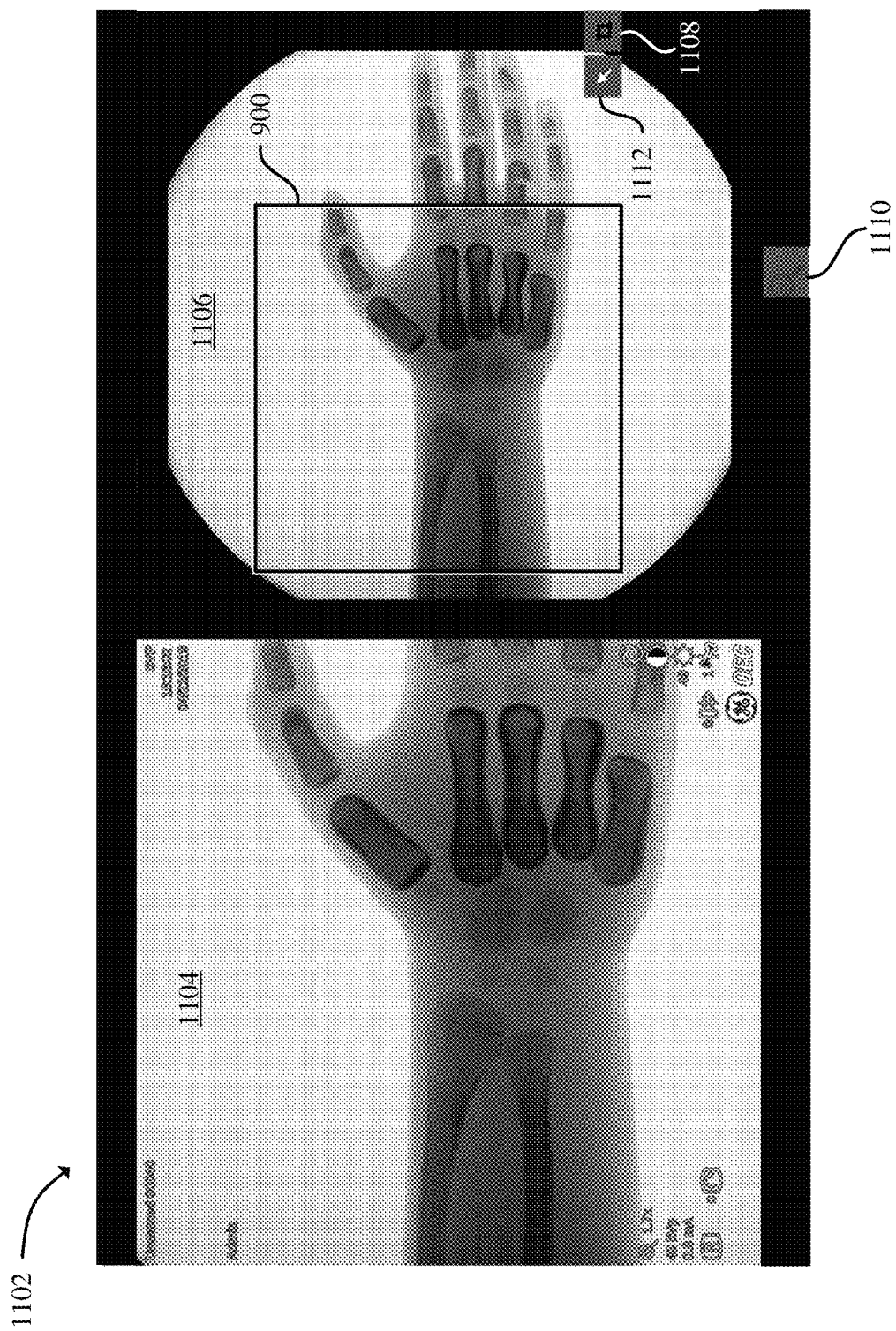
FIG. 13 depicts another graphical user interface with a roaming boundary that defines a region of interest in accordance with an exemplary embodiment.

In yet another embodiment, the configured processor determines the boundary based on a user input and in response, modifies a displayed reconstructed image. Briefly turning to FIGS. 11-13, in this embodiment the display 166 displays a GUI 1102 that includes first window 1104 and a second window 1106 that display a same reconstructed image. The GUI 1104 further includes a crop icon 1108, a zoom icon 1110, and a roam icon 1112. As depicted in FIG. 11, in response to a user selecting the crop icon 1108, the configured processor automatically applies a boundary 900 to the image displayed in the second window 1106 and automatically displays only the region of interest within the boundary 900 in the first window 1104. As depicted in FIG. 12, in response to a user selecting the zoom icon 1110, the configured processor automatically applies a boundary 900 to the image displayed in the second window 1106 and automatically displays the region of interest defined by the boundary 900 magnified by a given value in the first window 1104. As further depicted in FIG. 12, when the zoom icon 1110 is selected, the second window 1106 may also include a magnification slider 1202 that allows a user to modify an amount of magnification. As depicted in FIG. 13, in response to a user selecting the roam icon 1112, the configured processor automatically applies a boundary 900 to the image displayed in the second window 1106 and automatically displays the region of interest defined by the boundary 900 magnified by a given value. Furthermore, a user may use an external device 168 (i.e., a mouse, touchscreen, etc.) to move the boundary 900 and a corresponding region of interest is displayed in the second window 1106.

Returning to FIG. 8, at 808, the configured processor determines whether a modification to the overlaid boundary 900 is needed. The configured processor determines a modification to the overlaid boundary 900 is needed in response to a user modifying the overlaid boundary 900. A user may use an external device 168 (i.e., a mouse, touchscreen, etc.) to modify a shape, size, or position of the overlaid boundary 900. The configured processor determines modification to the overlaid boundary 900 is not needed in response to a user not modifying a boundary within a given time period.

Figure 14:
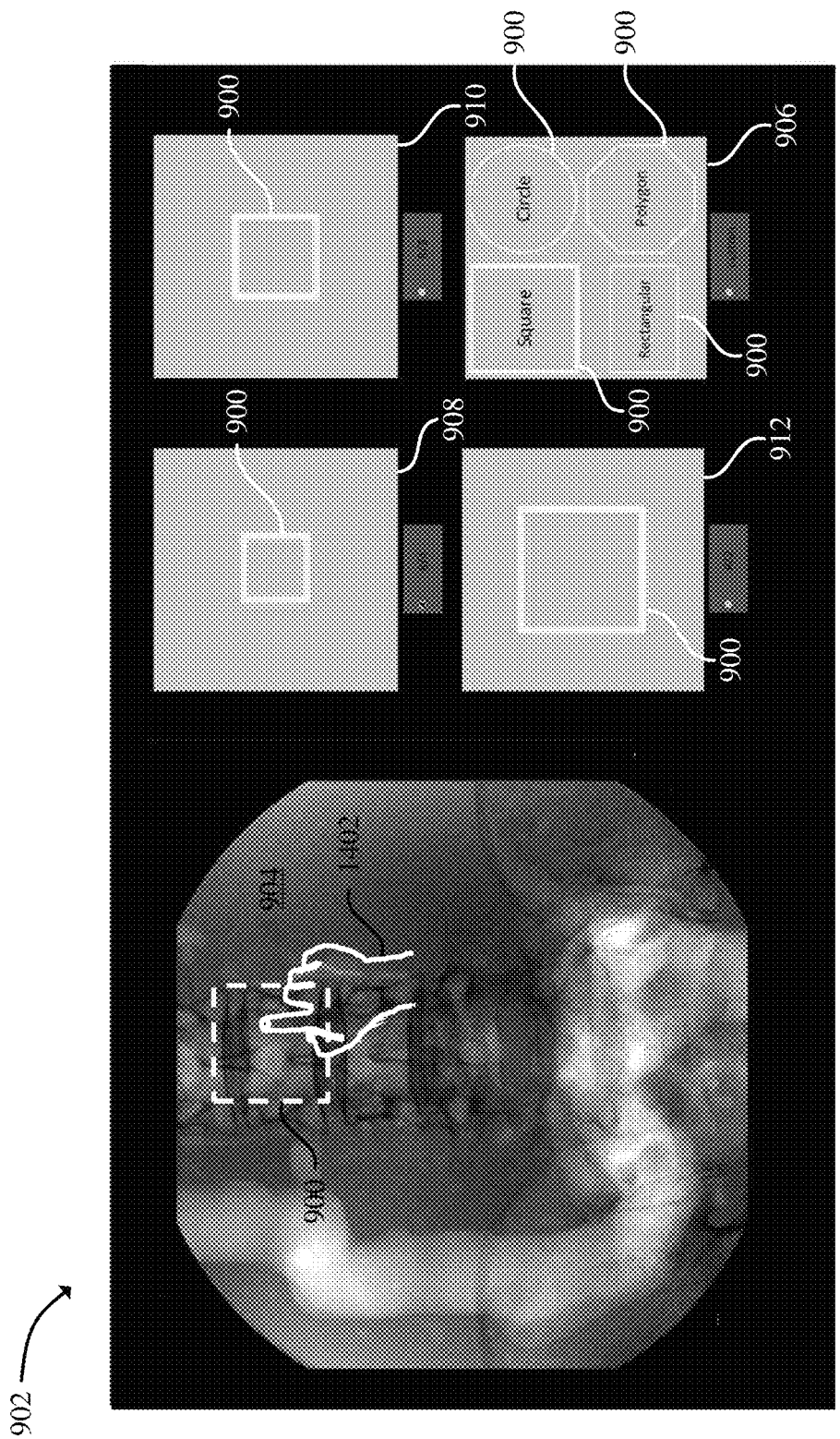
FIG. 14 depicts a user modifying a boundary that defines a region of interest in a graphical user interface in accordance with an exemplary embodiment.
Figure 15:
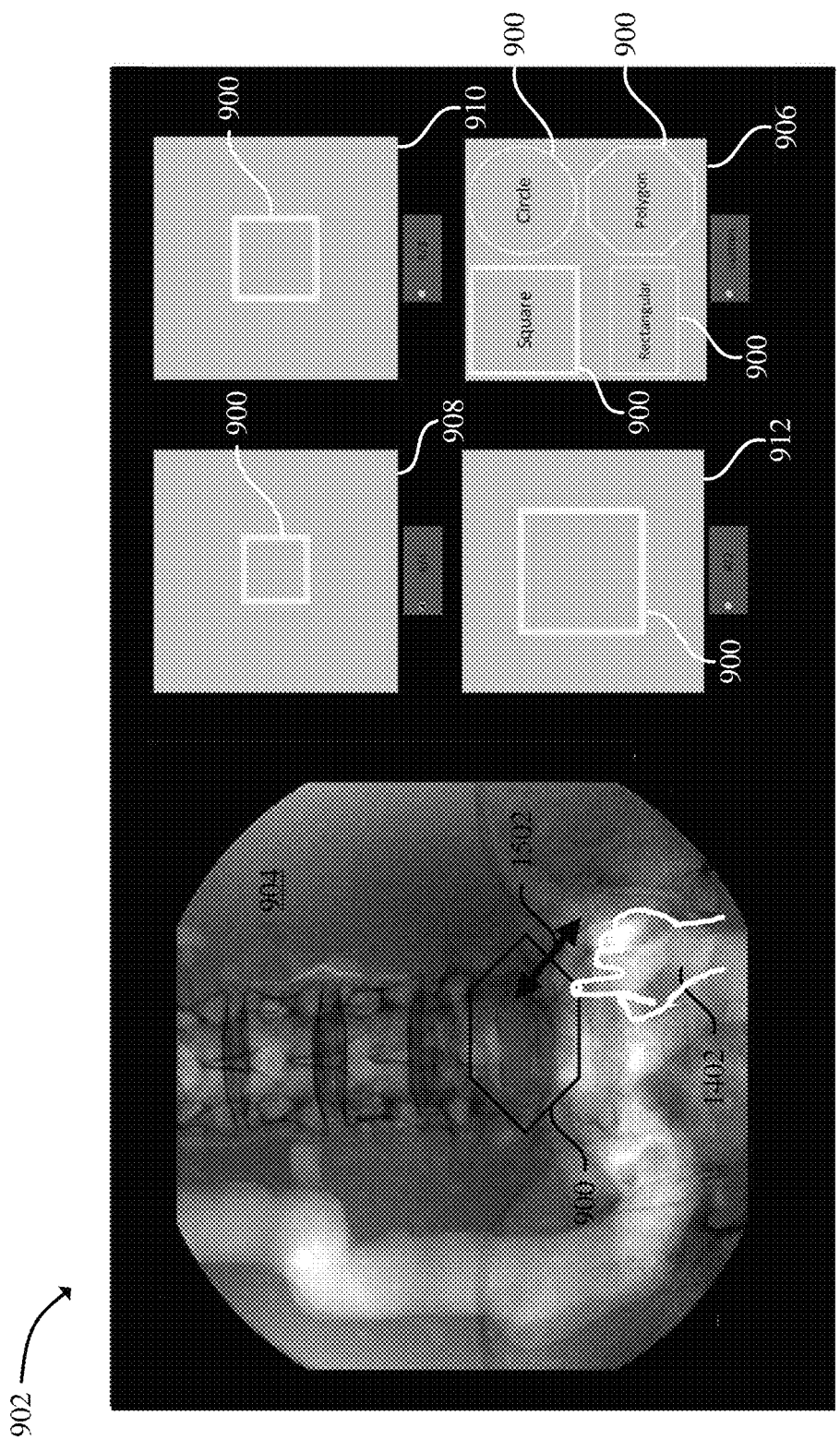
FIG. 15 depicts a user modifying a boundary that defines a region of interest in another graphical user interface in accordance with an exemplary embodiment.

Briefly turning to FIGS. 14 and 15, a user 1402 interacting with the GUI 902 is depicted in accordance with an exemplary embodiment. In the embodiment shown in FIGS. 14 and 15, the GUI 902 is displayed in a touchscreen. As depicted in FIG. 14, the user 1402 may move the boundary 900 by touching the region of interest defined by the boundary 900 and dragging the boundary 900 from a first location (i.e., the location depicted in FIG. 9) and to a second location (i.e., the location depicted in FIG. 14). As depicted in FIG. 15, the user 1402 may modify the shape boundary 900 by touching a side or a corner of the boundary 900 and dragging the selected side or corner of the boundary 900 from a first position to a second position (i.e., in one of the directions depicted by arrow 1502). While FIGS. 14 and 15 depict the user 1402 using a touch screen to modify the boundary 900, in another embodiment, the user 1000 may similarly use another external device 168 (i.e., a mouse) to modify the boundary 900. Furthermore, while FIGS. 14 and 15 depict the user 1402 modifying the boundary 900 in the GUI 902, the user 1402 may similarly move the boundary 900 displayed in the GUIs 1002 and 1102.

Returning to FIG. 8, at 810 in response to determining a modification to the overlaid boundary 900 is needed, the configured modifies the boundary 900 based on the user input and proceeds to 812.

In response to determining a modification to the overlaid boundary 900 is not needed, the configured processor proceeds to 812.

At 812, the configured processor enhances the region of interest within the boundary 900 thereby generating an enhanced region of interest. The configured processor may enhance the region of interest by applying a denoising algorithm and/or an automatic brightness and contrast adjustment algorithm to the region of interest. When an automatic brightness and contrast adjustment algorithm is applied to the region of interest, the configured processor determines a brightest and darkest pixel within the region of interest and sets the darkest pixel as 0 and sets the brightest pixel (i.e., most white) as N on a grayscale ranging from 0-N. In one embodiment, wherein a grayscale is defined as ranging from 0-255, the brightest pixel has a value of 255. Furthermore, each pixel within the region of interest of interest is then assigned a grayscale value between 0 and N relative to the darkest and brightest pixel within the region of interest.

Figure 17:
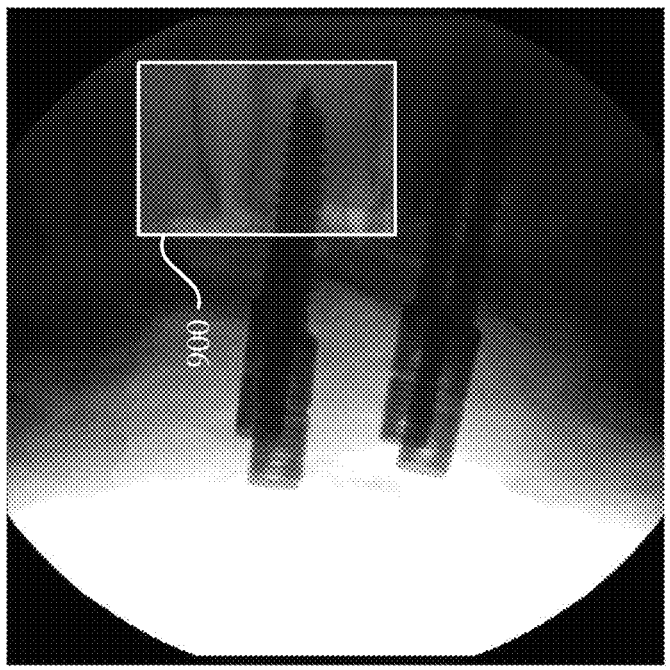
FIG. 17 depicts a region of interest within a boundary that has been enhanced in accordance with an exemplary embodiment.
Figure 16:
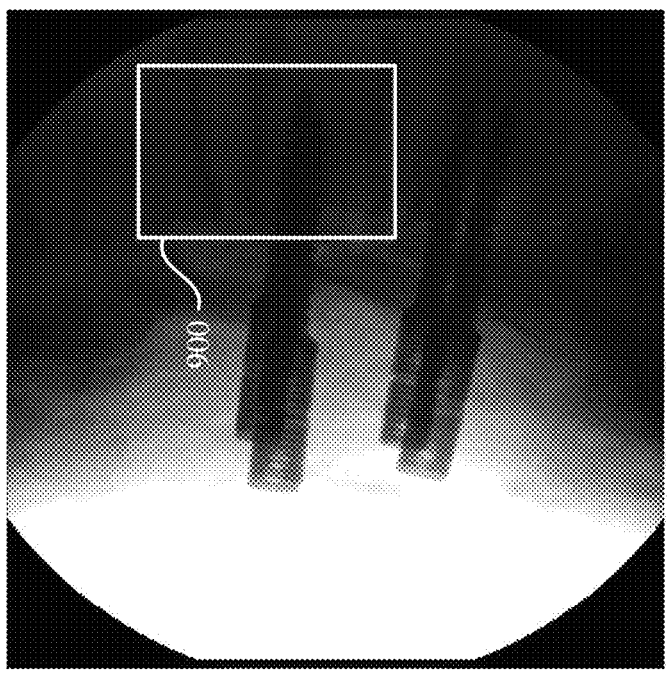
FIG. 16 depicts a region of interest within a boundary that has not been enhanced in accordance with an exemplary embodiment.

Briefly turning to FIG. 16, a reconstructed image with an overlaid boundary 900 is depicted in accordance with an exemplary embodiment. In FIG. 16, the region of interest within the boundary 900 has not been enhanced by a denoising algorithm and/or an automatic brightness and contrast adjustment algorithm. Turning to FIG. 17, reconstructed image with an overlaid boundary 900 is depicted in accordance with another exemplary embodiment. In FIG. 17, the region of interest within the boundary 900 has been enhanced by a denoising algorithm and an automatic brightness and contrast adjustment algorithm. In FIG. 17, the structures within the region of interest are easier to see relative to structures within the region of interest of FIG. 16 as the brightness and contrast of the region of interest in FIG. 17 has been adjusted.

Figure 18:
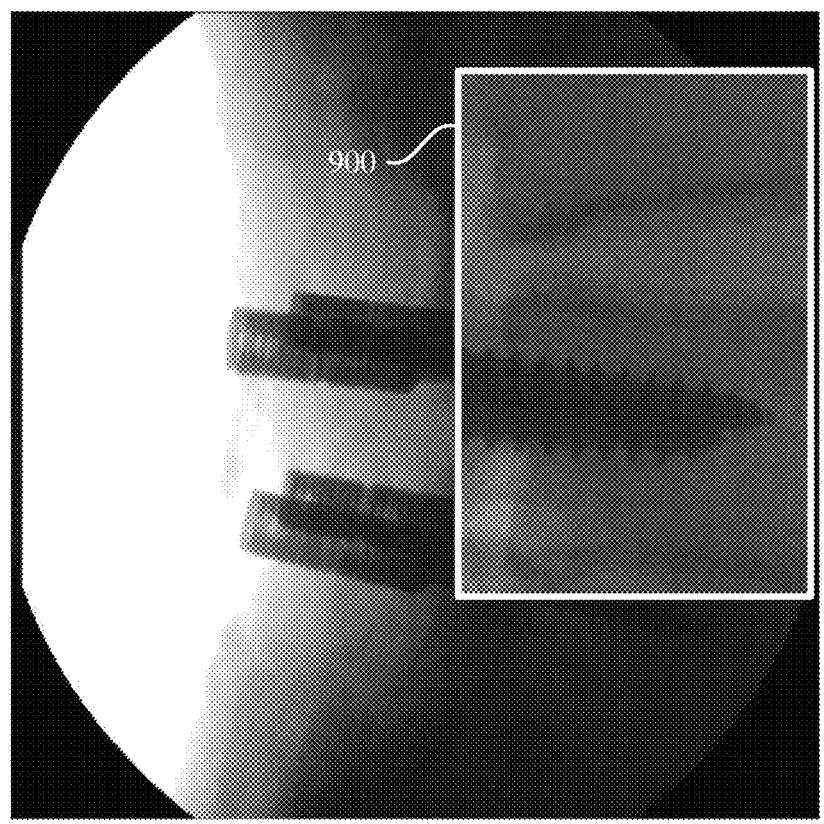
FIG. 18 depicts a region of interest within a boundary that has been enhanced and zoomed in on in accordance with an exemplary embodiment.

Returning to FIG. 8, at 814, the configured causes the display 166 to display the enhanced region of interest. In one embodiment, as depicted in FIG. 17, the enhanced region of interest replaces the region of interest defined by the boundary 900 and is embedded in the full reconstructed image. In another embodiment, as depicted in FIG. 18, the enhanced region of interest is magnified, replaces the region of interest defined by the boundary 900, and is embedded in the full reconstructed image. In yet another embodiment, the enhanced region of interest is cropped and shown in a separate window (i.e., in the first window 1104 of the GUI 1102). In yet another embodiment, the enhanced region of interest is zoomed in and shown in a separate window (i.e., in the first window 1104 of the GUI 1102).

Figure 19:
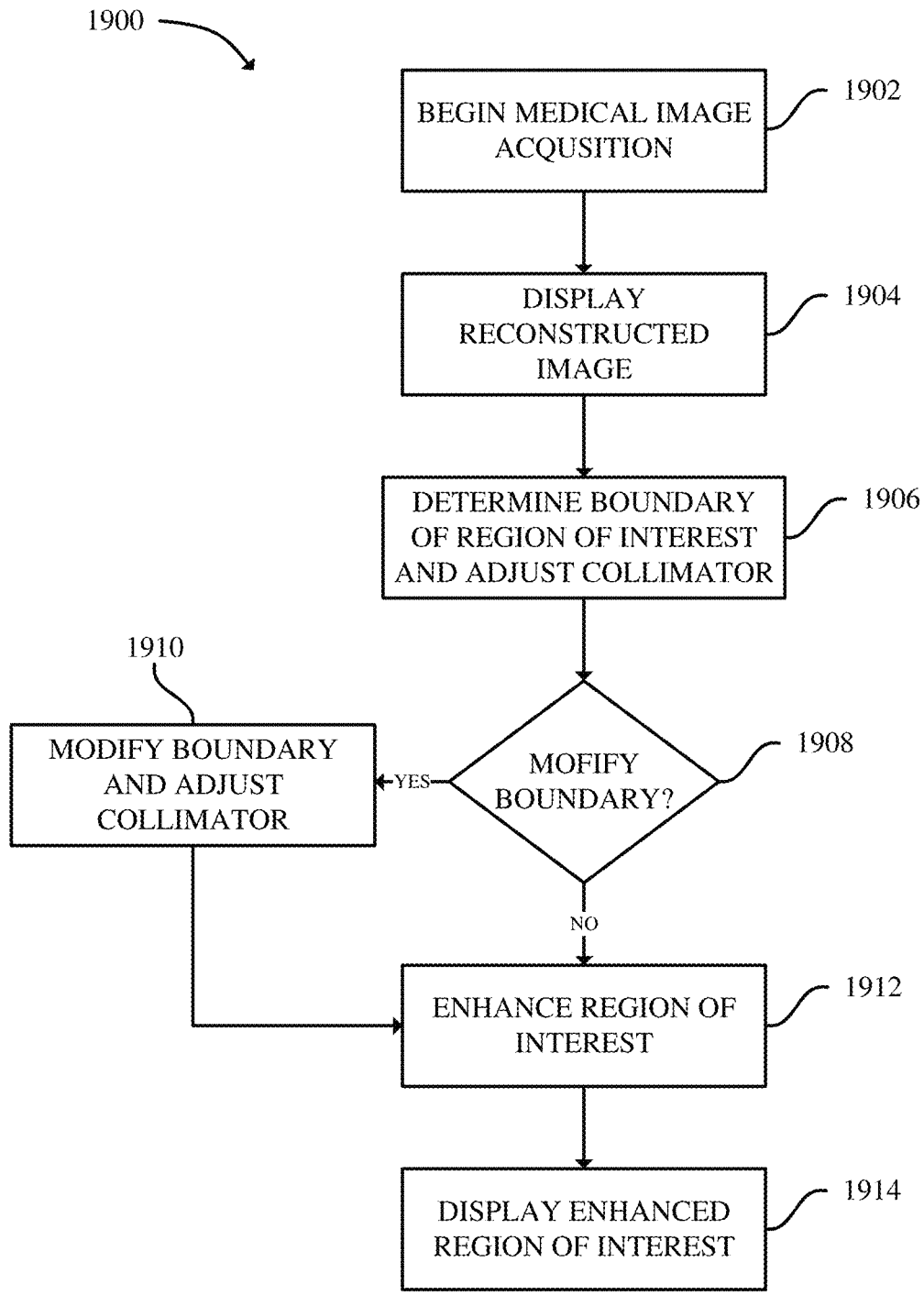
FIG. 19 is a flow chart of a method for locally enhancing a medical image and controlling a source collimator in accordance with an exemplary embodiment.

Referring now to FIG. 19, a method 1900 for enhancing an image and controlling a source collimator 124 is shown in accordance with an exemplary embodiment.

At 1902, a configured processor sends a signal to begin medical image acquisition to the control mechanism 146 and in response to receiving the signal to begin medical image acquisition, the control mechanism 146 causes the medical imaging system 100 to begin acquiring projection data of the patient 120 as previously described herein.

At 1904 the configured processor reconstructs a live image (i.e., an image that is reconstructed while the patient 120 is being exposed to radiation) from the projection data, sends the reconstructed image to the display 166, and in response to receiving the reconstructed image, the display 166 displays the image as previously described herein.

At 1906, the configured processor determines a shape and size of a boundary of a region of interest and overlays the determined boundary on a first displayed image as previously described herein. Furthermore, at 1906, the configured processor sends a signal to move the shutter 136 and the iris 138 of the source collimator 124 to the source collimator controller 154 as a function of the boundary 900. In response to receiving the signal to move the source collimator 124, the source collimator controller 154 moves the first collimator plates 140 and the second collimator plates 142 as previously described herein so that only the region of interest within the boundary 900 will be exposed to radiation as closely as possible.

Figure 20:
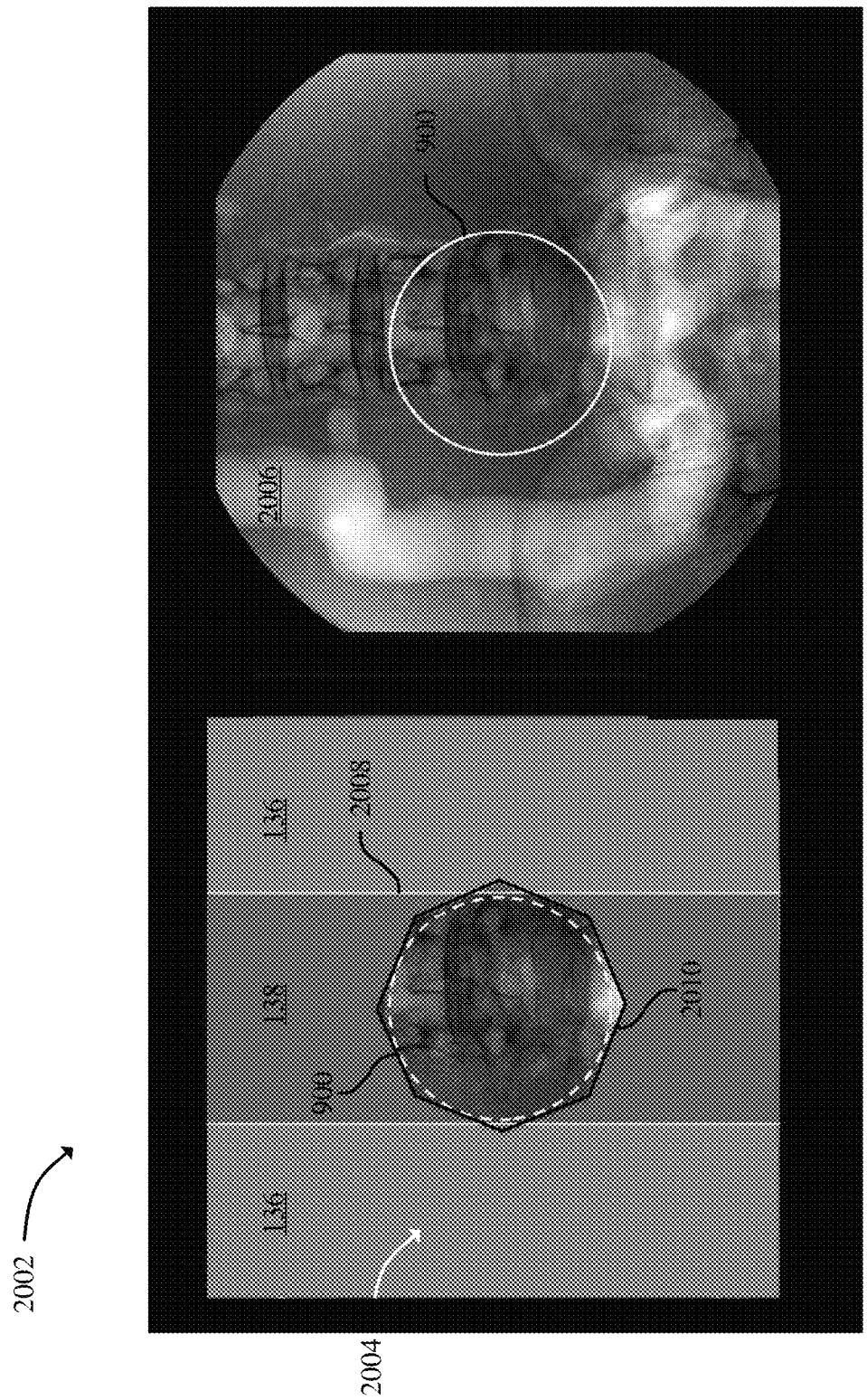
FIG. 20 depicts a graphical user interface that includes a circular boundary that defines a region of interest and a shutter and iris of a source collimator overlaid on a reconstructed image.

Also at 1906, the configured processor overlays an iris shape, a shutter shape, and the determined boundary on a second image such that only a region that will be exposed to radiation is shown based on a position of the shutter 136 and the iris 138. In some embodiments, the configured processor may also overlay a preview line of the iris and shutter. For example, as depicted in FIG. 20, a GUI 2002 displays a first window 2004 and a second window 2006. The first window 2004 and the second window 2006 display a circular boundary 900 overlaid on a reconstructed image. Furthermore, the first window 2004 displays the shutter 136 of the source collimator 124, a shutter preview line 2008, the iris 138 of the source collimator 124, and an iris preview line 2010. In this embodiment, the iris 138 is defined by eight second collimator plates 142 giving the iris 138 an octagonal shape. As depicted in the first window 2004, the collimator plates 140 of the shutter 136 have been moved such that the shutter preview line 2008 abuts the boundary 900 thereby limiting the area of the patient 120 that will be exposed to radiation.

Figure 21:
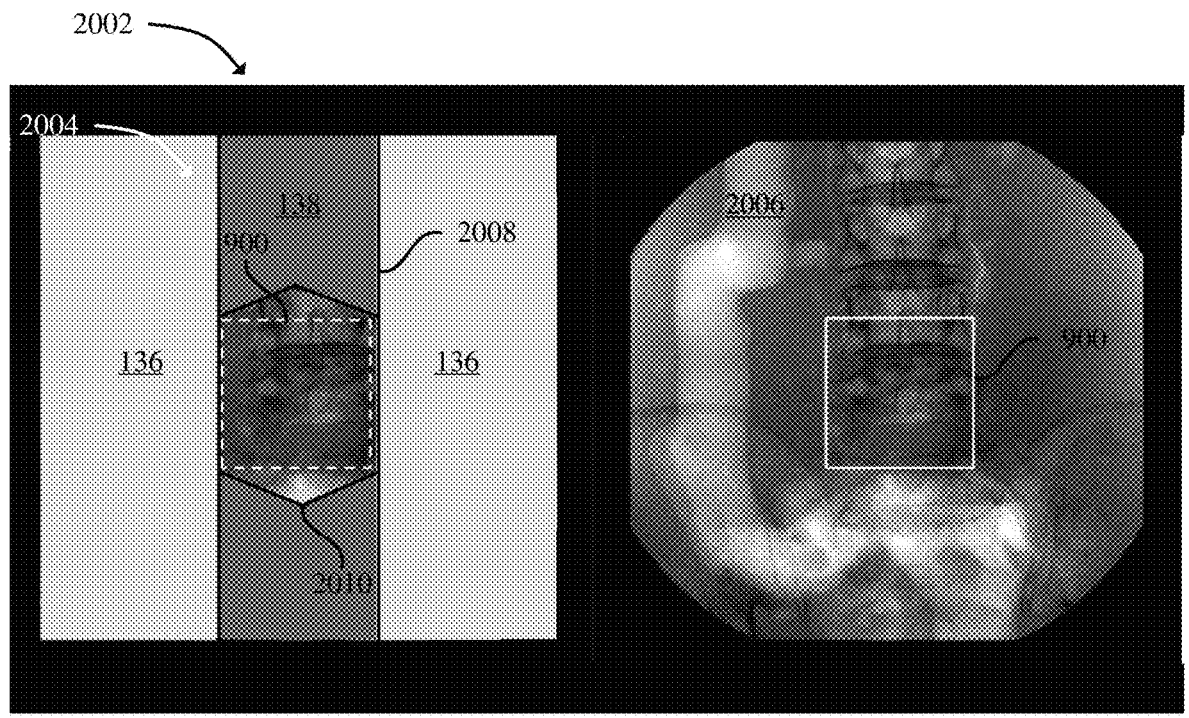
FIG. 21 depicts a graphical user interface that includes a square boundary that defines a region of interest and a shutter and iris of a source collimator overlaid on a reconstructed image.
Figure 22:
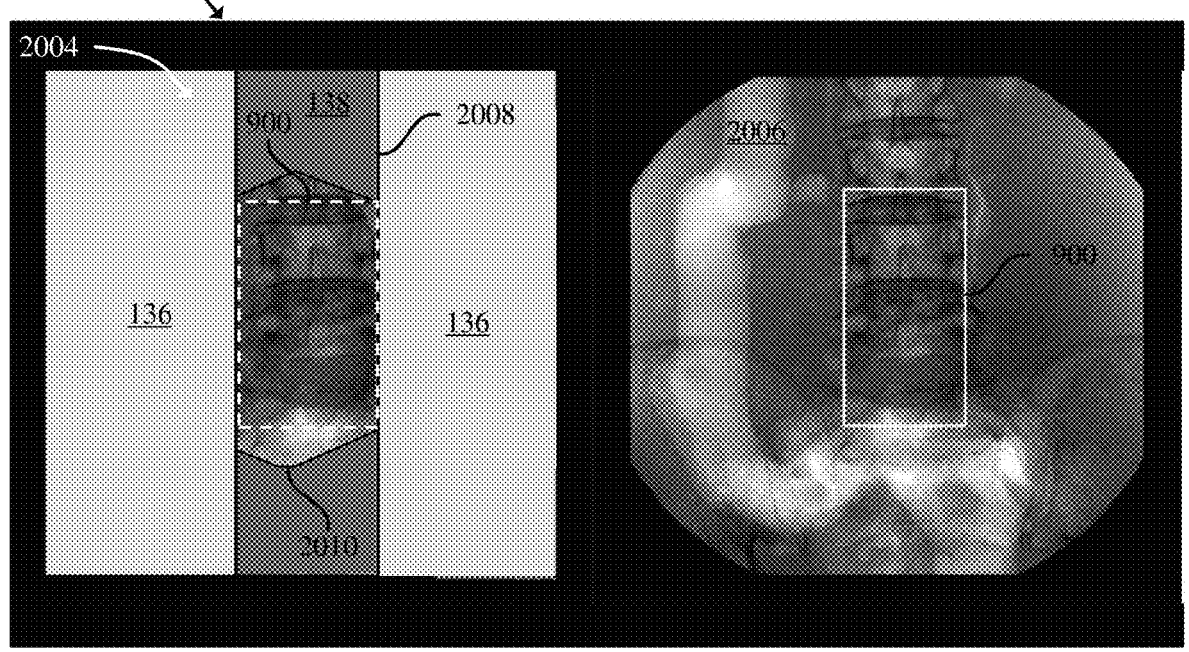
FIG. 22 depicts a graphical user interface that includes a rectangular boundary that defines a region of interest and a shutter and iris of a source collimator overlaid on a reconstructed image.

While FIG. 20 depicts a circular boundary 900 and an octagonal iris 138, in other embodiments the configured processor may overlay different sized and shaped boundaries 900 as previously discussed herein and the iris 138 may be formed of more or less second collimator plates 142 as previously discussed herein. In one example, as depicted in FIG. 21, the configured processor may overlay a square boundary 900 and the iris 138 may be defined by six second collimator plates 142. In another example, as depicted in FIG. 22, the configured processor may overlay a rectangular boundary 900 and the iris 138 may be defined by six second collimator plates 142.

Furthermore, a region of interest may be offset from a center of the reconstructed image displayed in the second window 2006. Accordingly, a center of a region of interest within a boundary 900 may be offset from the center of the reconstructed image by a distance ($\delta$). In this embodiment, the configured processor controls the second collimator plates 142 such that the aperture 144 of the source collimator 124 has radius defined by EQUATION 1:

$$R_{aperture} = R_{boundary} + \delta$$

wherein $R_{aperture}$ is the radius of the aperture 144, $R_{aperture}$ is the radius of a boundary 900 that defines a region of interest and $\delta$ is a distance that a center of the region of interest defined by the boundary 900 is offset from the center of the of the reconstructed image. In this embodiment, the radius of the iris 138 is measured from the center of the reconstructed image displayed in the first window 2004.

Figure 23:
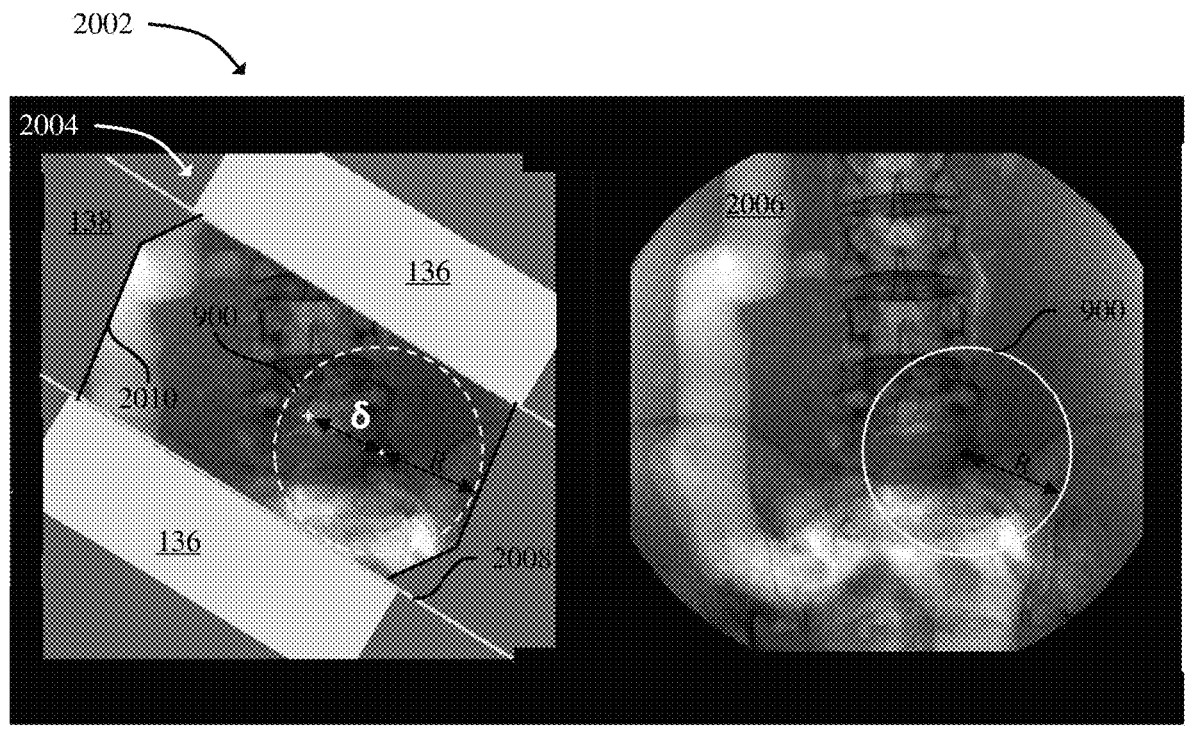
FIG. 23 depicts a graphical user interface that includes a circular boundary that defines a region of interest that is offset from a center of a reconstructed image and a shutter and iris of a source collimator overlaid on a reconstructed image.
Figure 24:
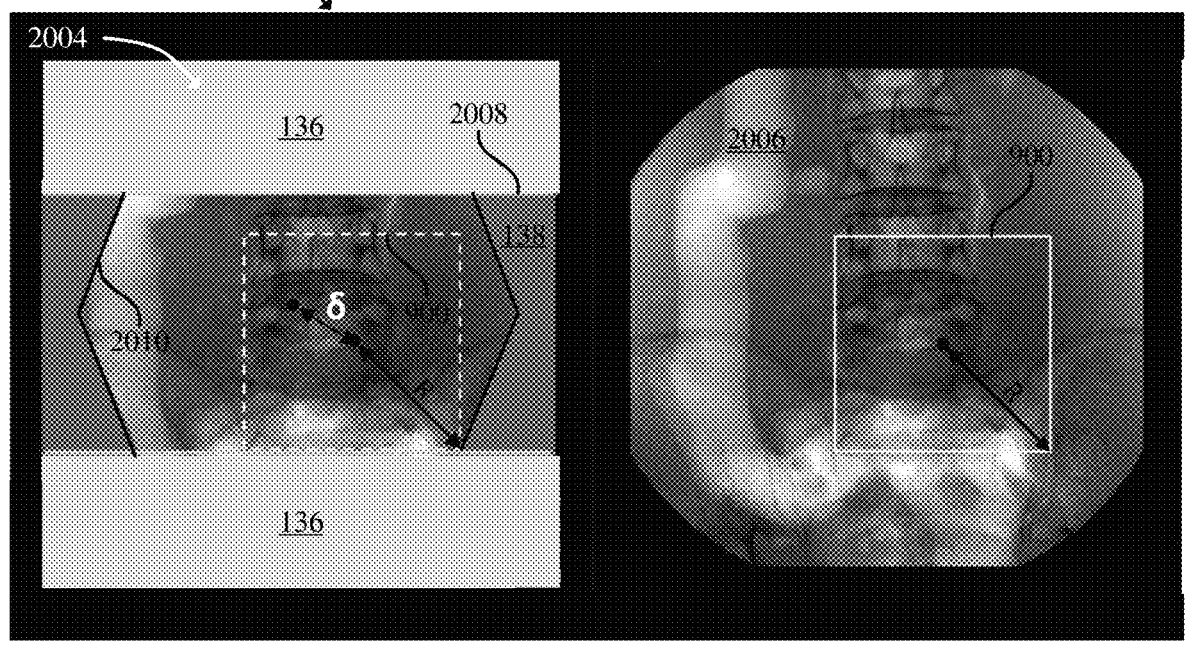
FIG. 24 depicts a graphical user interface that includes a square boundary that defines a region of interest that is offset from a center of a reconstructed image and a shutter and iris of a source collimator overlaid on a reconstructed image.
Figure 25:
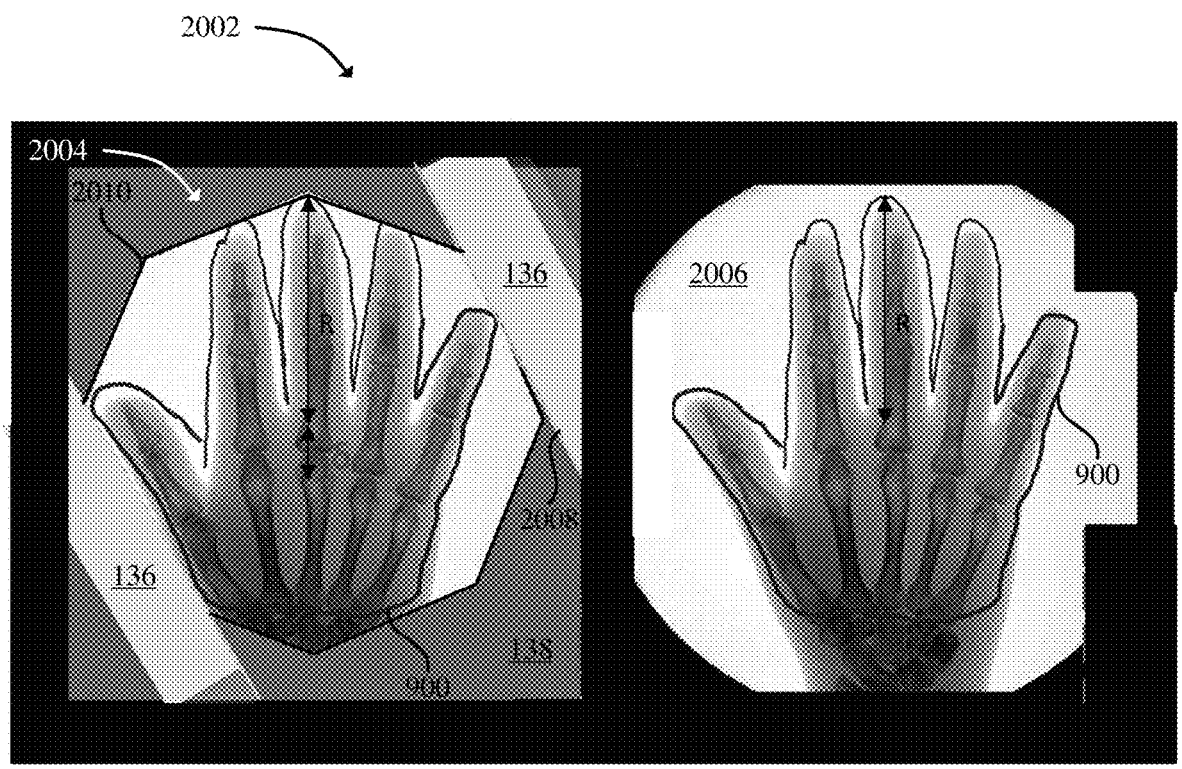
FIG. 25 depicts a graphical user interface that includes a user drawn boundary that defines a region of interest that is offset from a center of a reconstructed image and a shutter and iris of a source collimator overlaid on a reconstructed image.

FIGS. 23-25 depict embodiments wherein a boundary 900 of a region of interest is offset from a center of a reconstructed image displayed in the first window 2004 and the second window 2006. As depicted in FIGS. 23-25, the aperture 144 has a radius equal to the radius of the $R_{aperture} + \delta$.

Returning to FIG. 19, at 1908 the configured processor determines whether a modification to the overlaid boundary 900 is needed as previously discussed herein.

At 1910 in response to determining a modification to the overlaid boundary 900 is needed, the configured modifies the boundary 900 based on the user input previously discussed herein and sends a signal to move the shutter 136 and the iris 138 of the source collimator 124 to the source collimator controller 154 as a function of the modified boundary 900. In response to receiving the signal to move the source collimator 124, the source collimator controller 154 moves the first collimator plates 140 and the second collimator plates 142 as previously described herein so that only the region of interest within the modified boundary 900 will be exposed to radiation as closely as possible as previously discussed herein.

In response to determining a modification to the overlaid boundary 900 is not needed, the configured processor proceeds to 1912.

At 1912, the configured processor enhances the region of interest within the boundary 900 thereby generating an enhanced region of interest as previously discussed herein.

At 1914, the configured causes the display 166 to display the enhanced region of interest as previously discussed herein.

In addition to any previously indicated modification, numerous other variations and alternative arrangements may be devised by those skilled in the art without departing from the spirt and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation, and use may be made without departing from the principles and concepts set forth herein. Also, as used herein, the examples and embodiments are meant to be illustrative only and should not be construed to be limiting in any manner.

What is claimed is:

1. A method comprising:
   determining a boundary of a region of interest in a displayed medical image;
   overlaying the boundary on the displayed medical image;
   adjusting a position of a collimator of a medical imaging system based on the determined boundary;
   enhancing image quality of the region of interest; and
   displaying the enhanced region of interest within the boundary.

2. The method of claim 1, wherein the displayed medical image is a live image.

3. The method of claim 1 wherein the medical imaging system includes a C-arm that carries a radiation source and a radiation detector.

4. The method of claim 1, further comprising:
   acquiring projection data with the medical imaging system; and
   reconstructing the projection data to generate the displayed medical image.

5. The method of claim 1, wherein adjusting the position of the collimator includes:
adjusting a position of a shutter of the collimator; and
adjusting a position of an iris of the collimator.

6. The method of claim 1, wherein the boundary is determined based on a user input.

7. The method of claim 6, wherein the user input includes a user selecting a predetermined boundary or drawing the boundary on the displayed medical image.

8. The method of claim 1, further comprising:
modifying the boundary based on a user input; and
adjusting the position of the collimator based on the modified boundary.

9. The method of claim 8, wherein modifying the boundary includes moving the boundary from a first position to a different second position.

10. The method of claim 8, wherein modifying the boundary includes moving a side or a corner of the boundary.

11. The method of claim 1, further comprising:
determining a radius of an aperture of the collimator based on a radius of the determined boundary and a distance between a center of the region of interest within the boundary from a center of the displayed image; and
adjusting the position of the collimator based on the determined radius.

12. The method of claim 1, wherein enhancing image quality of the region of interest includes denoising and adjusting a brightness and contrast of the region of interest based on grayscale pixel values within the region of interest.

13. A system comprising:
a processor;
a computer readable storage medium in communication with the processor, wherein the processor executes computer readable instructions stored in the computer readable storage medium which cause the processor to:
determine a boundary of a region of interest in a displayed medical image;
overlay the boundary on the displayed medical image;
adjust a position of a collimator of a medical imaging system based on the determined boundary;
enhance image quality of the region of interest; and
display the enhanced region of interest within the boundary.

14. The system of claim 13, wherein the image is a live image.

15. The system of claim 13, wherein the boundary is determined based on a user input.

16. The system of claim 14, wherein the user input includes a user selecting a predetermined boundary or drawing the boundary on the displayed medical image.

17. The system of claim 13, wherein the instructions further cause the processor to:
modify the boundary based on a user input; and
adjust the position of the collimator based on the modified boundary.

18. The system of claim 13, wherein the instructions further cause the processor to:
determine a radius of an aperture of the collimator based on a radius of the determined boundary and a distance between a center of the region of interest within the boundary from a center of the displayed image; and
adjust the position of the collimator based on the determined radius.

19. The system of claim 13, wherein enhancing image quality of the region of interest includes denoising and adjusting a brightness and contrast of the region of interest based on grayscale pixel values within the region of interest.

20. A computer readable storage medium with computer readable program instructions that, when executed by a processor, cause the processor to:
determine a boundary of a region of interest in a displayed medical image;
overlay the boundary on the displayed medical image;
adjust a position of a collimator of a medical imaging system based on the determined boundary;
enhance image quality of the region of interest; and
display the enhanced region of interest within the boundary.

* * * * *